United States Patent [19]

Shofner et al.

[11] Patent Number: 5,533,145
[45] Date of Patent: Jul. 2, 1996

[54] CONTINUOUS TWO DIMENSIONAL MONITORING OF THIN WEBS OF TEXTILE MATERIALS

[75] Inventors: Frederick M. Shofner; Joseph C. Baldwin, both of Knoxville, Tenn.

[73] Assignee: Zellweger Uster, Inc., Knoxville, Tenn.

[21] Appl. No.: 329,660

[22] Filed: Oct. 26, 1994

Related U.S. Application Data

[63] Continuation of Ser. No. 999,114, Dec. 31, 1992, abandoned.

[51] Int. Cl.[6] .............................. G06K 9/00; B07C 5/00; G01N 21/86; G01V 9/04
[52] U.S. Cl. .................. 382/141; 209/576; 250/559.42; 336/239; 336/328
[58] Field of Search .......................... 382/1, 8, 28, 141, 382/100, 206, 207; 250/571; 209/576–577, 580–582, 590; 356/23, 36, 238–239, 326–328, 429

[56] References Cited

U.S. PATENT DOCUMENTS

| | | | |
|---|---|---|---|
| 4,253,765 | 3/1981 | Kato et al. | 356/328 |
| 4,375,919 | 3/1983 | Busch | 356/326 |
| 4,561,018 | 12/1985 | Berthel et al. | 358/107 |
| 4,619,527 | 10/1986 | Leuenberger et al. | 356/238 |
| 4,714,340 | 12/1987 | Stillwagon | 356/23 |
| 4,784,275 | 11/1988 | Fridge | 209/558 |
| 4,786,817 | 11/1988 | Boissenvain et al. | 250/571 |
| 4,837,715 | 6/1989 | Ungpiyakul et al. | 364/552 |
| 4,890,924 | 1/1990 | Beckstein | 356/429 |
| 4,951,825 | 8/1990 | Hawkins et al. | 209/558 |
| 4,963,035 | 10/1990 | McCarthy et al. | 382/28 |
| 5,012,681 | 5/1991 | Lentzen | 73/863.23 |
| 5,044,380 | 9/1991 | Crooks et al. | 131/329 |
| 5,054,930 | 10/1991 | Adelson | 356/429 |
| 5,068,799 | 11/1991 | Jarrett, Jr. | 364/507 |
| 5,073,857 | 12/1991 | Peters et al. | |
| 5,087,120 | 2/1992 | Anthony | 356/36 |
| 5,125,514 | 6/1992 | Oehler et al. | 209/590 |
| 5,190,163 | 3/1993 | Anzai et al. | 209/588 |

FOREIGN PATENT DOCUMENTS

| | | | |
|---|---|---|---|
| 1377453 | 12/1974 | Australia | G01N 9/00 |
| 484029 | 7/1947 | Belgium | G01N 33/36 |
| 422616A2 | 4/1991 | European Pat. Off. | G01N 15/14 |
| 462424 | 3/1937 | United Kingdom | G01N 33/36 |
| 1242171 | 8/1971 | United Kingdom | D01H 1/12 |
| 9114169 | 9/1991 | WIPO | G01N 15/14 |

OTHER PUBLICATIONS

*Advanced Fiber Information System: A New Technology of Evaluating Cotton*, Frederick M. Shofner, Gordon F. Williams, C. Kenneth Bragg and Preston E. Sasser.

Yu, F. T. S., "Principles of Optical Engineering." 1990, John Wiley & Sons, pp. 59–66.

*Primary Examiner*—Joseph Mancuso
*Assistant Examiner*—Gerard Del Rosso
*Attorney, Agent, or Firm*—Luedeka, Neely & Graham

[57] ABSTRACT

An apparatus monitors a web of textile material which is also processed by a textile processing machine. The web is in motion relative to an imaging unit, and the imaging unit repetitively scans at least one strip across the web in a direction substantially perpendicular to the direction of relative motion of the web. A computer receives signals from the imaging unit and produces digital data corresponding thereto. The computer further analyzes the digital data to find entities of interest in the web and determines parameters of the found entities of interest. Preferably, the imaging unit and computer include distinguishing means for producing a plurality of optical images of the same portion of the web where each of the optical images are distinguished one from the others by the spectral content. In addition, the imaging unit and computer produce a plurality of time separated images, where each of the time separated images are produced during different lighting conditions on the web. In one embodiment, one image is produced while the front side of the web is illuminated, and another image is produced on the same portion of the web while the rear side of the web is illuminated.

17 Claims, 21 Drawing Sheets

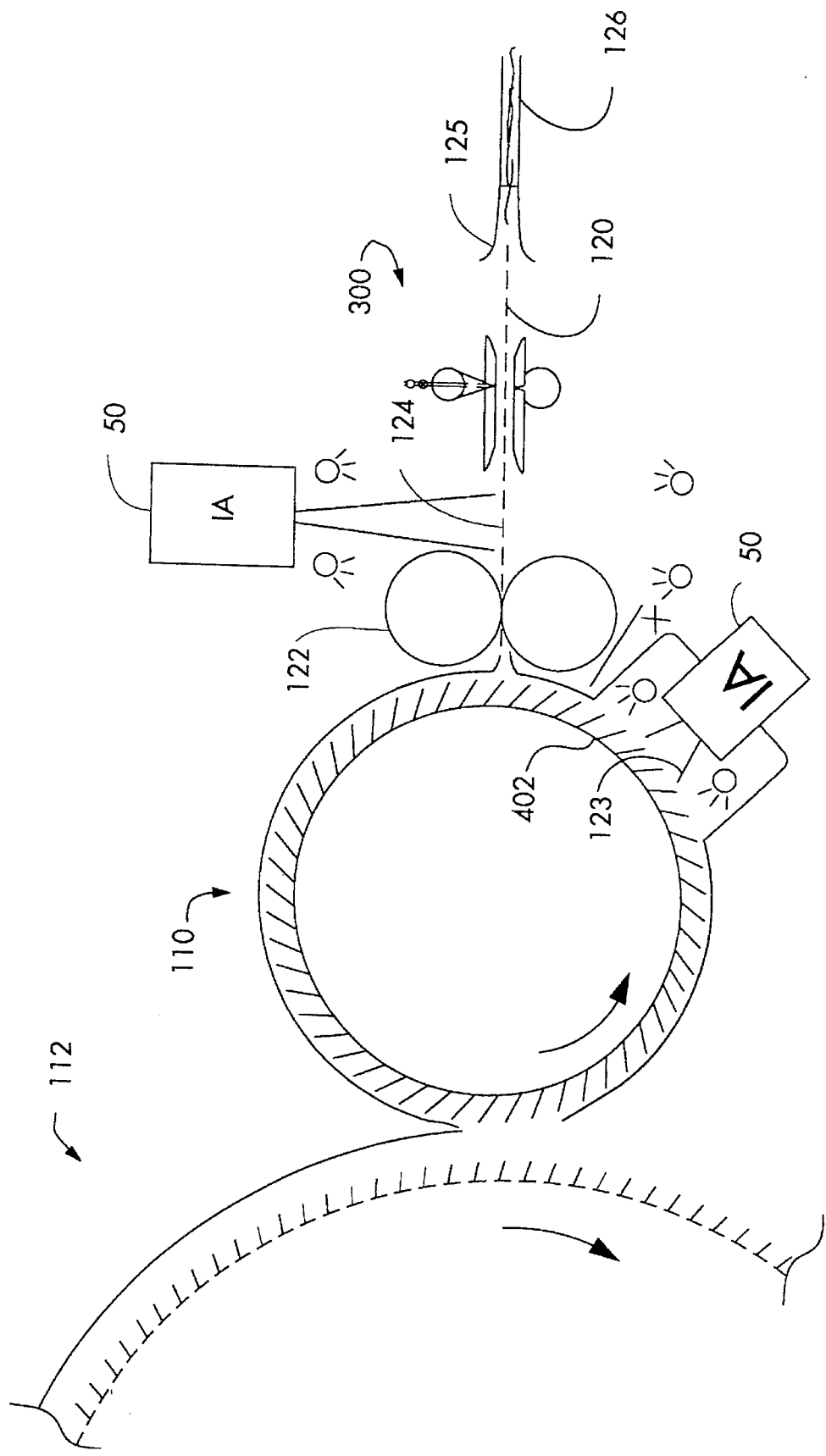

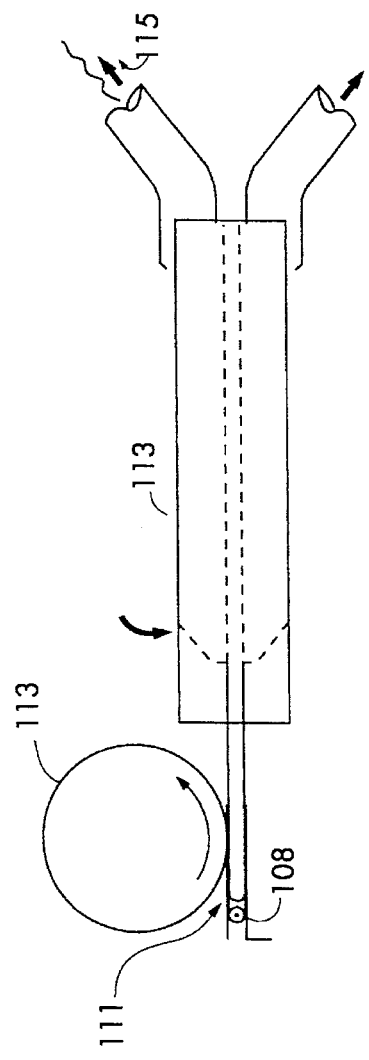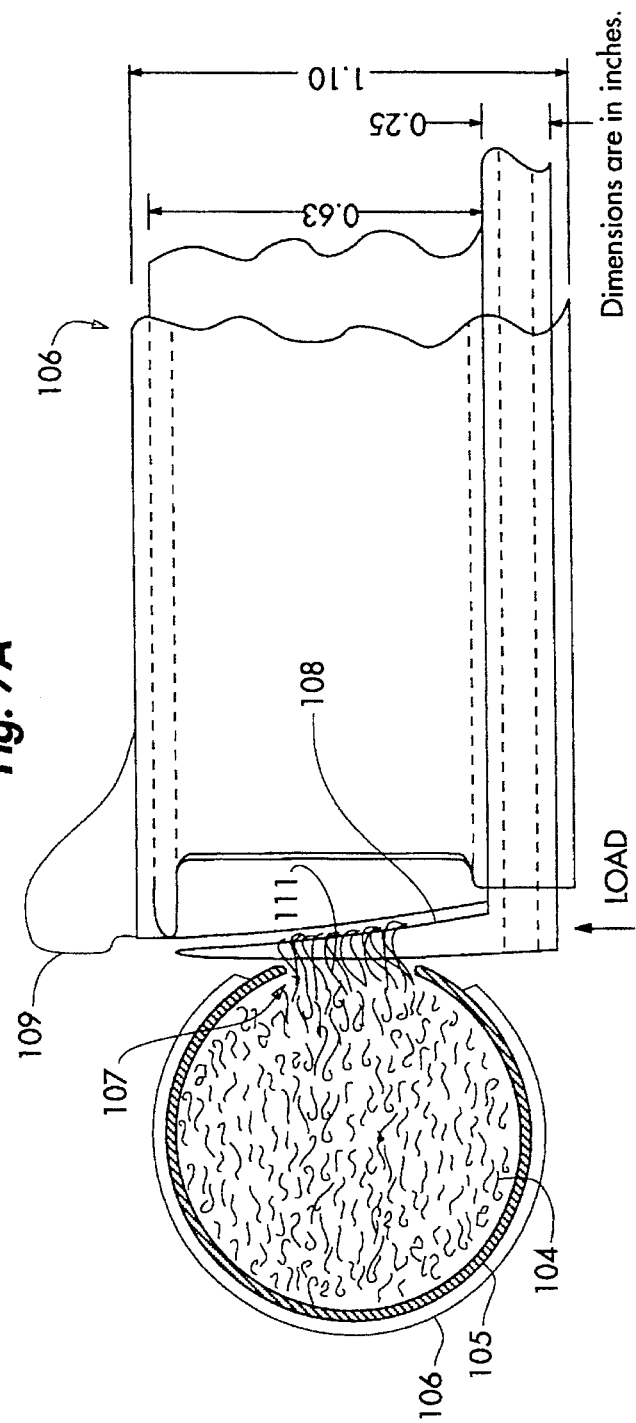

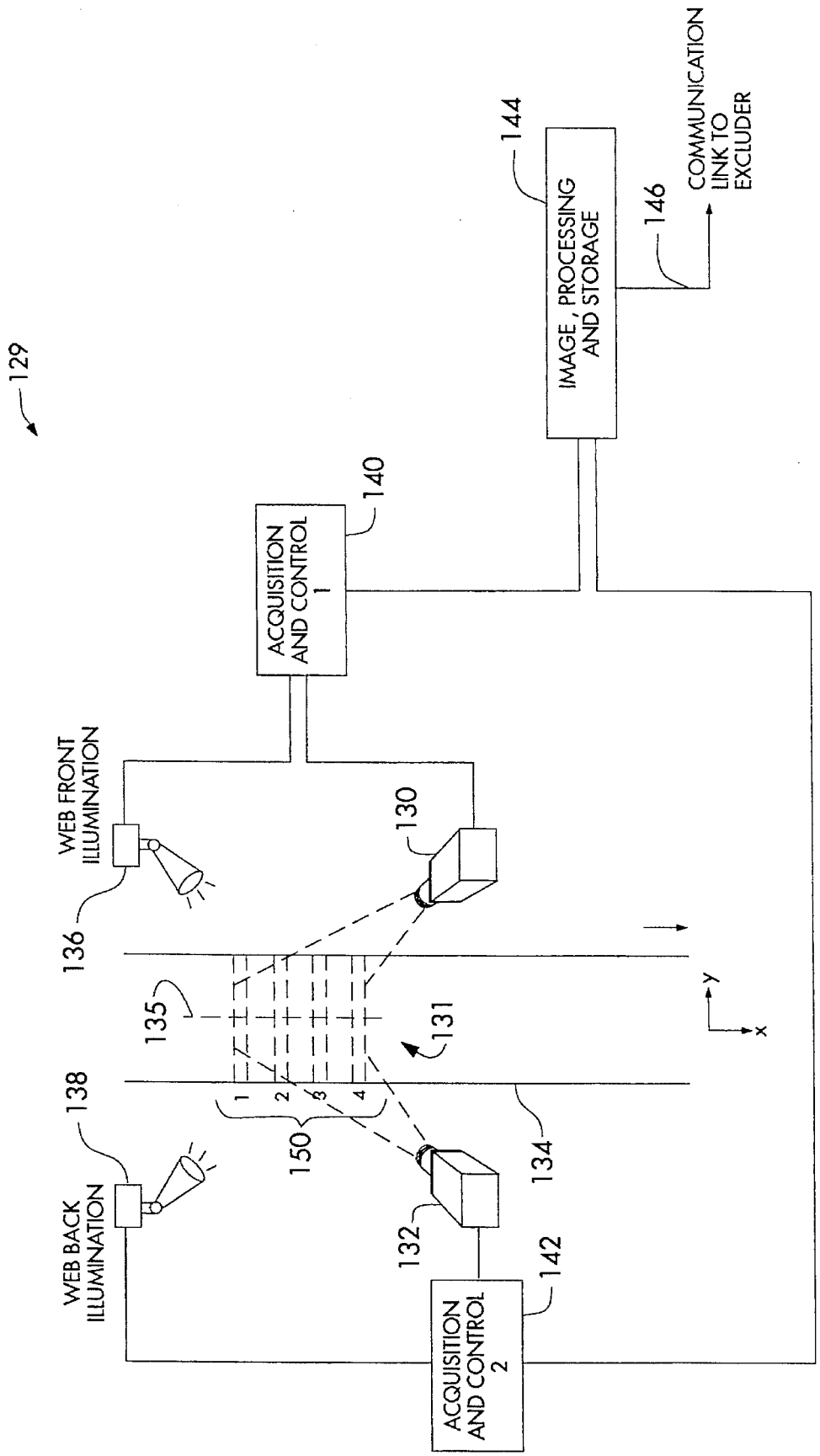

Fig. 12A
Fig. 12B
Fig. 12C
Fig. 12D

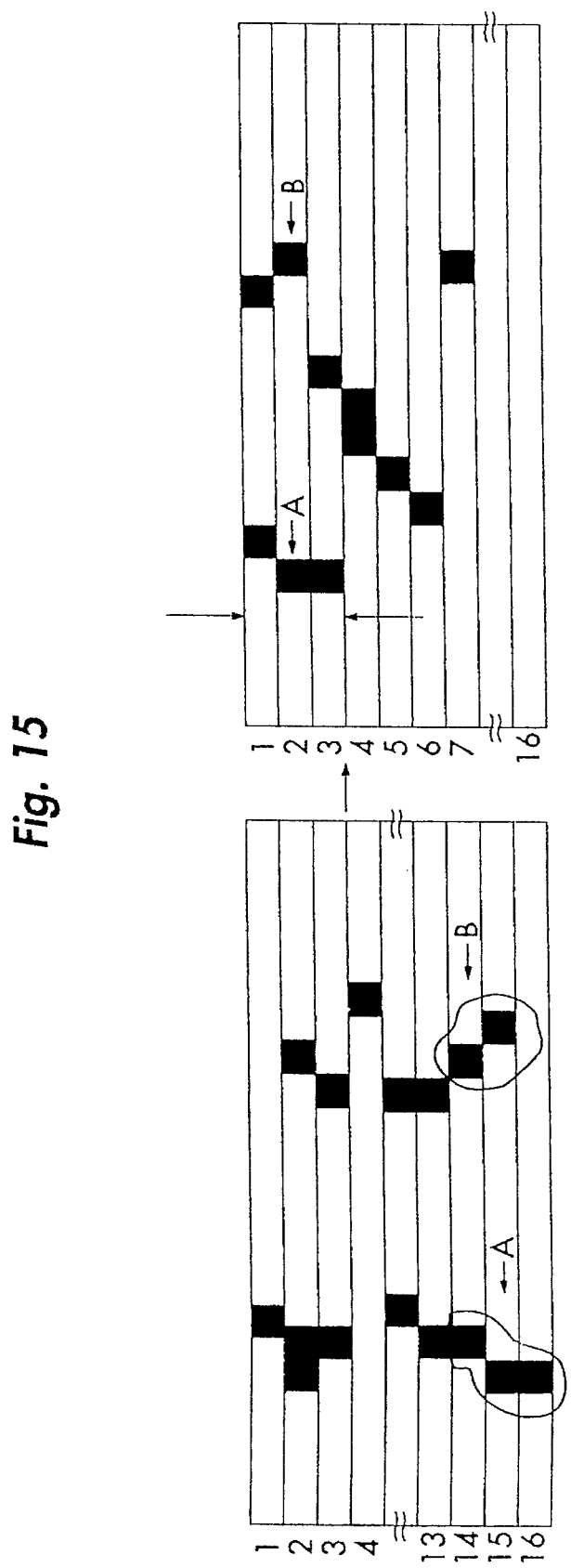

CONTINUOUS TWO DIMENSIONAL MONITORING OF THIN WEBS OF TEXTILE MATERIALS

This is a continuation, of application Ser. No. 07/999, 114, filed Dec. 31, 1992 now abandoned.

FIELD OF THE INVENTION

The present invention relates to methods and apparatus for the in-process, real-time measurement and control of entities in thin webs of textile materials. In the preferred embodiment, such entities include single fibers, single neps, and single trash particles in cotton and other fibrous materials. Neps are defined as any of the little knots formed by irregular growth of cotton fibers or by the rubbing together of the fibers especially in ginning, or a cluster of fibers occurring in wool staple. The thin webs are either intentionally formed from a sample of material acquired from the process or inherently found within certain processing machines. Measurement is by image analysis preferably based on charge-coupled device (CCD) cameras with extended spectral response.

To further define the field of this invention, means are provided for acquisition of in-process samples from continuously-operating textile manufacturing process machinery. Image analysis then enables spatial, spectral, and temporal pattern recognition or filtering (SSTF). SSTF in turn enables identification of individual entities in the thin webs.

BACKGROUND OF THE INVENTION

The presence of undesirable entities in textile materials such as neps and trash particles is a problem whose severity is generally increasing. Production and harvesting techniques of cotton, for example, demand more aggressive cleaning action at the gin or in the early stages of processing in the textile mill. These actions remove foreign matter or trash but in many cases break the trash into smaller particles and leave some of it in the fibrous mass. This makes it more difficult to remove in later stages. Worse, this increasingly aggressive cleaning action generally increases the level of nep formation. It is therefore increasingly important to monitor the levels of these undesirable entities on a continuous basis in the gin or mill in order to optimally control them.

In most production environments it is completely impossible to monitor 100% of the process throughput and samples of in-process material must be acquired for measurement. In most textile processing machines the fiber samples conveniently available for sampling are in tuft form. New means are therefore needed to acquire a representative sample and prepare it into thin web format for image analysis measurement. There are notable exceptions where judicious application of recently-developed image analysis technology enable 100% monitoring of the process throughput. A good example, as will be disclosed below in a preferred embodiment, is monitoring the thin web of a carding machine. Prior art methods and apparatus result in overwhelmingly expensive or otherwise impractical applications of image analysis. Our invention overcomes the difficulties.

SUMMARY OF THE INVENTION

In accordance with the present invention, on-line monitoring is provided for controlling the quality of card web. Undesirable entities are Found in preferably 100% of the thin card web, Identified as to the severity of their impact upon subsequent processes or ultimately on sale price of the textile product derived therefrom, and then prioritized control action is taken to remove or exclude these entities from the web. These web-cleaning provisions are identified by the acronym "FIX".

In accordance with a particular aspect of the present invention, an apparatus is provided for monitoring a web of textile materials. The web may be monitored while it is being processed by textile processing machinery, or it may be formed seperately from the textile processing machinery. The web includes a plurality of entities, such as fibers and trash. An imaging unit receives electromagnetic radiation from the web and produces image signals in response thereto. The image signals correspond to images of the web including the entities, and the web is in motion relative to the imaging unit. The imaging unit repetitively scans at least one stripe across the web in a direction substantially perpendicular to the direction of the relative motion of the web. A computer receives the image signals from the imaging units and produces digital data corresponding thereto. The computer analyzes the digital data and finds entities of interest in the web based on the analysis of such data. The computer further determines parameters of the found entities of interest and produces output signals indicating parameters of the entities of interest in the web.

In accordance with another aspect of the present invention, the imaging unit and computer further include distinguishing apparatus, such as a spectral grating or prism, for producing a plurality of optical images of the same portion of the web from the received electromagnetic radiation, where each of the optical images is distinguished from the others by the spectral content of the images. The computer produces a plurality of digital data representations corresponding to the plurality of optical images and analyzes the digital data to find images of entities of interest. The computer also determines the spectral content of the received electromagnetic radiation produced by the entity of interest based on the analysis of the plurality of digital data representations.

In accordance with another aspect of the present invention, the imaging unit further includes apparatus for producing a plurality of time separated images of the same portion of the web. In the preferred embodiment, a mask is disposed for receiving electromagnetic radiation from the web, for blocking portions of the electromagnetic radiation and for transmitting at least first and second spatially separated portions of the electromagnetic radiation. Imaging optics focus images of the first and second spatially separated portions of the electromagnetic radiation onto an array of detectors which produce image signals corresponding to the first and second spatially separated portions of the electromagnetic radiation.

In accordance with another aspect of the present invention, the imaging unit produces at least first and second time separated images of the same portion of the web. The first time separated image is produced while the web is illuminated by a first illuminating condition, and the second time separated image is produced while the web undergoes a second illuminating condition which is different than the first illuminating condition. In one embodiment, the first illuminating condition is illumination of the front side of the web and the second illuminating condition is illumination of the back side of the web. The computer also classifies entities according to the apparent size of the entity, the apparent shape of the entity and the apparent color of the entity.

BRIEF DESCRIPTION OF THE DRAWINGS

The present invention may best be understood by reference to the following Detailed Description of preferred embodiments when considered in conjunction with the drawing in which:

FIG. 6 is a cross-sectional view illustrating an implementation of the present invention in conjunction with a web on a doffer cylinder and/or a web as it leaves the doff rolls of a textile machine;

FIG. 7A is a somewhat diagrammatical cross-sectional view of a tube containing a sliver of textile fibers being sampled by a needle sampler;

FIG. 7B is a schematic diagram of a processing station where fiber samples are removed from the needle sampler of FIG. 7A;

FIG. 8 shows a block diagram of an optical imaging system including two CCD cameras, and front and back illumination of a web;

FIG. 12 illustrates four books of memory into which images from the CCD are stored;

FIG. 15 is a graphical illustration of two images in the image buffer;

DETAILED DESCRIPTION OF A PREFERRED EMBODIMENT

WEB FORMING SAMPLER

Figure 1:
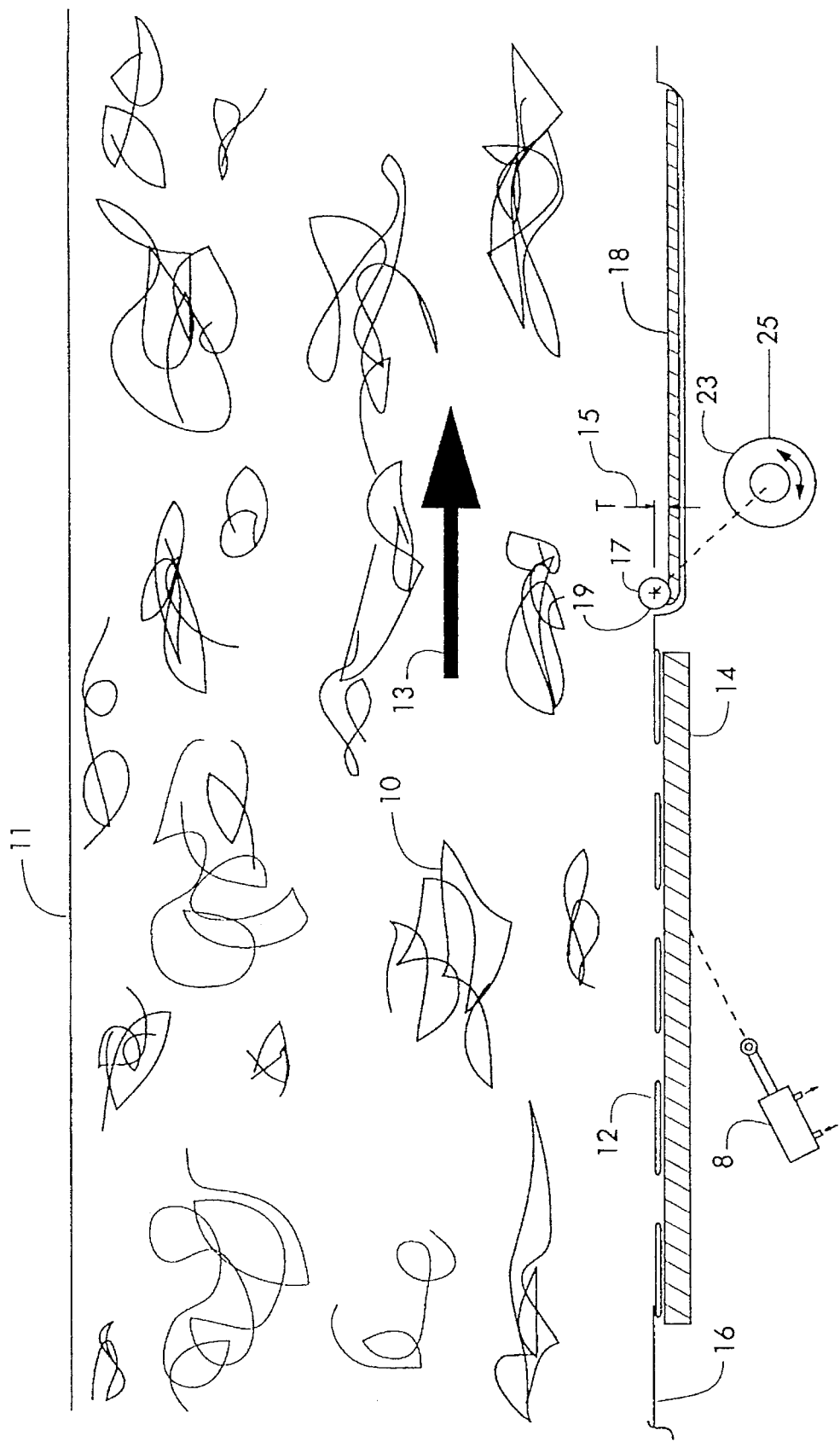
FIG. 1 is a somewhat diagrammatical cross-sectional view of tufts of fibers being transported pneumatically within a duct and showing a sampler in a wall of the duct.
Figure 2:
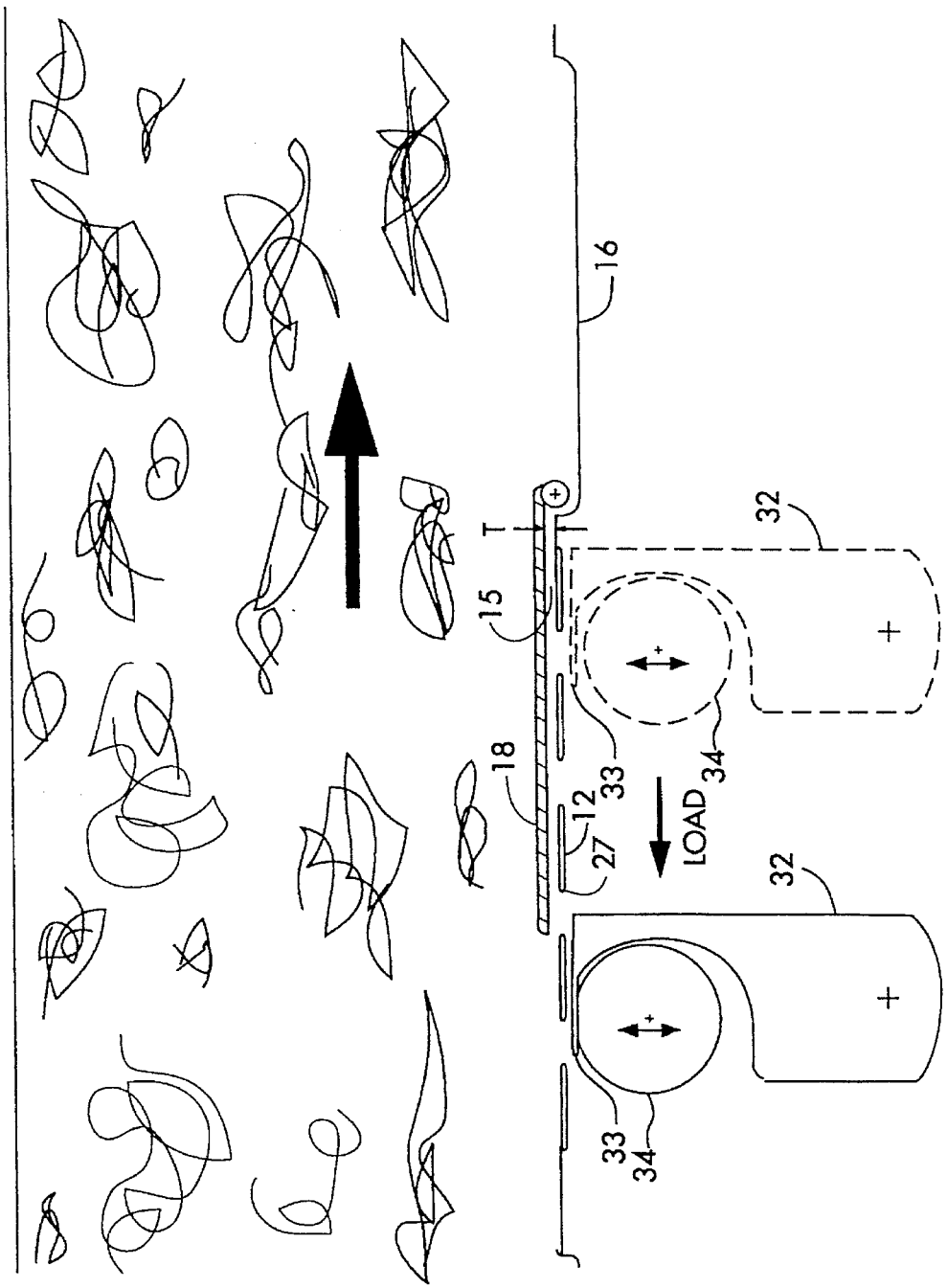
FIG. 2 is an illustration similar to FIG. 1 showing a sampler in operation removing samples of fiber from the duct.

FIG. 1 illustrates tufts of fiber 10 being transported pneumatically within a duct 11 in a direction indicated by arrow 13. On one side of the duct there is placed a perforated wall 12 in combination with a solid cover plate 14 to seal against the perforated wall and against the solid sides of the duct 11. This cover plate 14 overcomes pressure differentials between the inside and outside of the duct 11. Sampler plate 18, shown in stowed position in FIG. 1, is mounted on a drive mechanism 17, such as a hydraulic motor and control system, and is rotated about an axis 19 upon command from a control signal on line 21 into the flow, thus capturing tufts 10 which are impacted upon it. In the course of rotating counter-clockwise into the flow, impacted tufts 10 of suitable amount are collected and ultimately moved into a closed position by the rotary motion of the plate 18, as shown in FIG. 2. After plate 18 moves to the closed position shown in FIG. 2, the sealing plate 14 is removed by a suitable mechanical mechanism 23, such as a hydraulic piston and cylinder and control system, to expose the perforated wall 12, when appropriate control signals are applied through control lines 25.

FIG. 2 illustrates that the sampling plate 18 has come to sampling position over the perforated plate 12. The sealing plate 14 has been retracted since the combined action of the fiber sample 20 on the perforated plate 12 and the sealing action of the sampling plate can withstand the pressure differential between the inside and outside of the duct 11.

As a result of this action, a fiber sample 20 is presented through the perforated plate holes 27 for sampling by a needle sampler 32, which is further described in a co-pending application entitled "Needle Based Apparatus for Individualizing Fibers and Other Textile Entities for Testing Purposes" filed Dec. 31, 1992. In the right-hand side of the lower part of FIG. 2 there is shown, in broken line format, a needle sampler 32' with the locking/feed roll 34' in the retracted or open position. The needle sampler 32' (broken line) is just beginning its right to left motion The row of needles 33', whose width into the paper is about 2 to 4 inches, move in close proximity to the perforated plate 12 and thereby acquires samples of entities 20 from the perforated holes 27 until the sampler 32 has been loaded and moved fully to the left. At this point the needle sampler 32 locking/feed roll 34 is closed, as shown in solid lines in the lower left side of FIG. 2, and the sample loading step has been completed. In this figure the roll 34 is intended to represent a conventional locking feed roll that rotates around its center axis and/or moves linearly in response to rotate and/or translate control signals.

The sampler 32 is carried by a suitable mechanism for translating it horizontally and rotating it downwardly. Preferably, the sampler 32 is fixedly mounted on an arm 35 extending from hydraulic motor 37. A carriage 39 is mounted on a linear chain drive and rails 36, and the carriage 39 carries the motor 37 through horizontal motion on the rails 36. A motor and motor control system 38 under control of signals on lines 39 provide motive force to the chain drive and rails 36 to drive the carriage 39 and motor 37 to thereby move the sampler 32 between the positions indicated by solid line sampler 32 and the broken line sampler 32'. In addition, under control from signals on line 43, the motor 37 selectively rotates the sampler in the direction indicated by arc 45.

Figure 3:
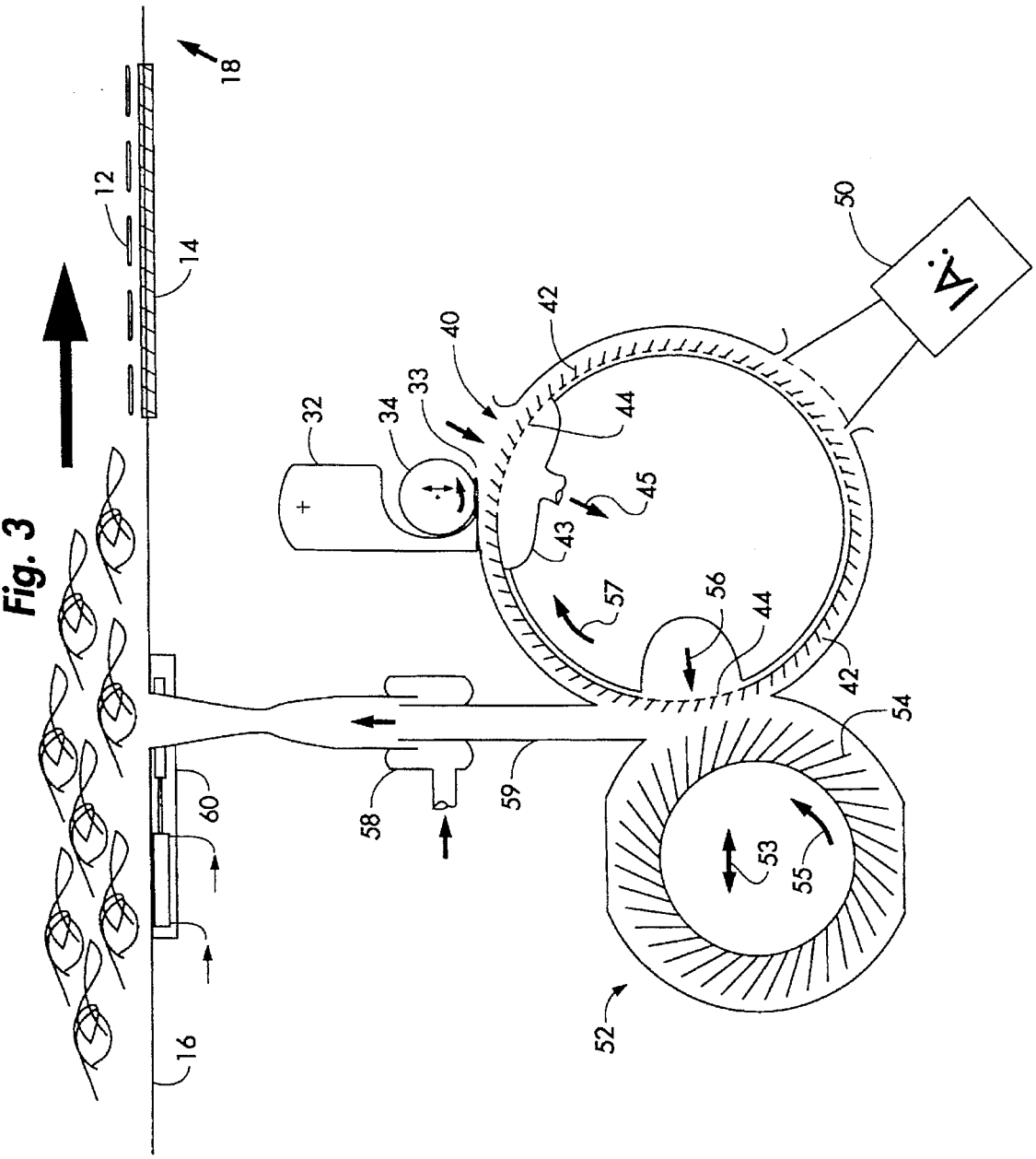
FIG. 3 is a somewhat diagrammatical drawing further illustrating the operation of the sampler and showing the sampler delivering fibers to a cylinder.

As shown in FIG. 3, the needle sampler 32 has been rotated and translated away from the sampling position which is adjacent to the perforated plate 12. The sealing plate 14 is moved back into a closed position as shown in FIG. 1 and the sampling plate 18 is rotated clockwise back into its stow position. The fibers which were captured on sampling plate 18 are blown away by compressed air and re-injected into the pneumatic conveying air in duct 16.

FIG. 3 further illustrates that the needle sampler has been rotated into registration with presentation cylinder 40. Cylinder 40, which preferably includes pins 42 and perforations 44 on its surface, combs and aligns the fibers and serves as a presentation device for the thin web of fibers and other entities deposited thereupon. (The thin web is not shown.) Fibers are uniformly released from the pins 33 by rotating the locking/feed roll 34 in the fiber sampler 32 in concert with rotation of the thin web presentation cylinder 40 so that fibers are uniformly deposited onto the cylinder 40. A plenum 43 and suction 45 on the plenum provide a suction through perforations 44 to assist the deposition of fibers from sampler 32 onto cylinder 40. The first objective of this transfer step is to transfer 100% of the fiber sample, including all entities in the sample such as neps or trash, without substantial modification. The second objective is forming the sample into the thin web format desired for presentation to the image analysis system 50. Further details of needle sampler 32, alternative needle sampling means, and alternative measurement means are disclosed in co-pending application entitled "Needle Based Apparatus for Individualizing Fibers and Other Textile Entities for Testing Purposes" filed Dec. 31, 1992, which is incorporated herein by reference. Preferably, approximately 1 gram of sample is transferred from each needle sample 32 to the presentation cylinder 40. This quantity is associated with a needle sampler 32 width of approximately 4 inches.

The presentation cylinder 40 presents a thin web of entities for examination by image analysis means 50. In the embodiment of FIG. 3, fine pins 42 and perforations 44 on cylinder 40 are used to assure uniform removal and loading as well as to assure some combing and separation actions of the sample as it is removed from the needles 33. The image analysis means 50 thus examine a thin web which has been deposited in a preferred manner. Consideration is given to uniformity and orientation of fibrous entities in the material sample as will be fully disclosed hereinafter.

Before explaining the image analysis or control dimensions of this invention, completion of the sampling cycle is explained. Upon completion of the image analysis measurement by means 50, the brush 52 is moved to the right as indicated by arrows 53 such that the bristles 54 engage the pins 42. The brush 52 and the presentation cylinder 40 are rotated as shown by arrows 55 and 57 whereupon the fibers, neps, trash, and other entities are removed from the presentation cylinder 40 by the combined action by the brush 52 and compressed air 56 applied through the perforated holes 44. A coaxial adductor 58 is used to supply suction through conduit 59 with which to drive airflow from the brush 52 and presentation cylinder 40 region back into the pneumatic conveying process duct 11. Upon completion of this action, slide valve 60 closes. The system is now prepared for another measurement sequence. In the above description, mechanical movements and control are accomplished by conventional means and preferably the entire operation is under control of a conventional microprocessor based controller or a computer, such as the computer system 144 of FIG. 8, but each step may be manually controlled, if desired.

Figure 4:
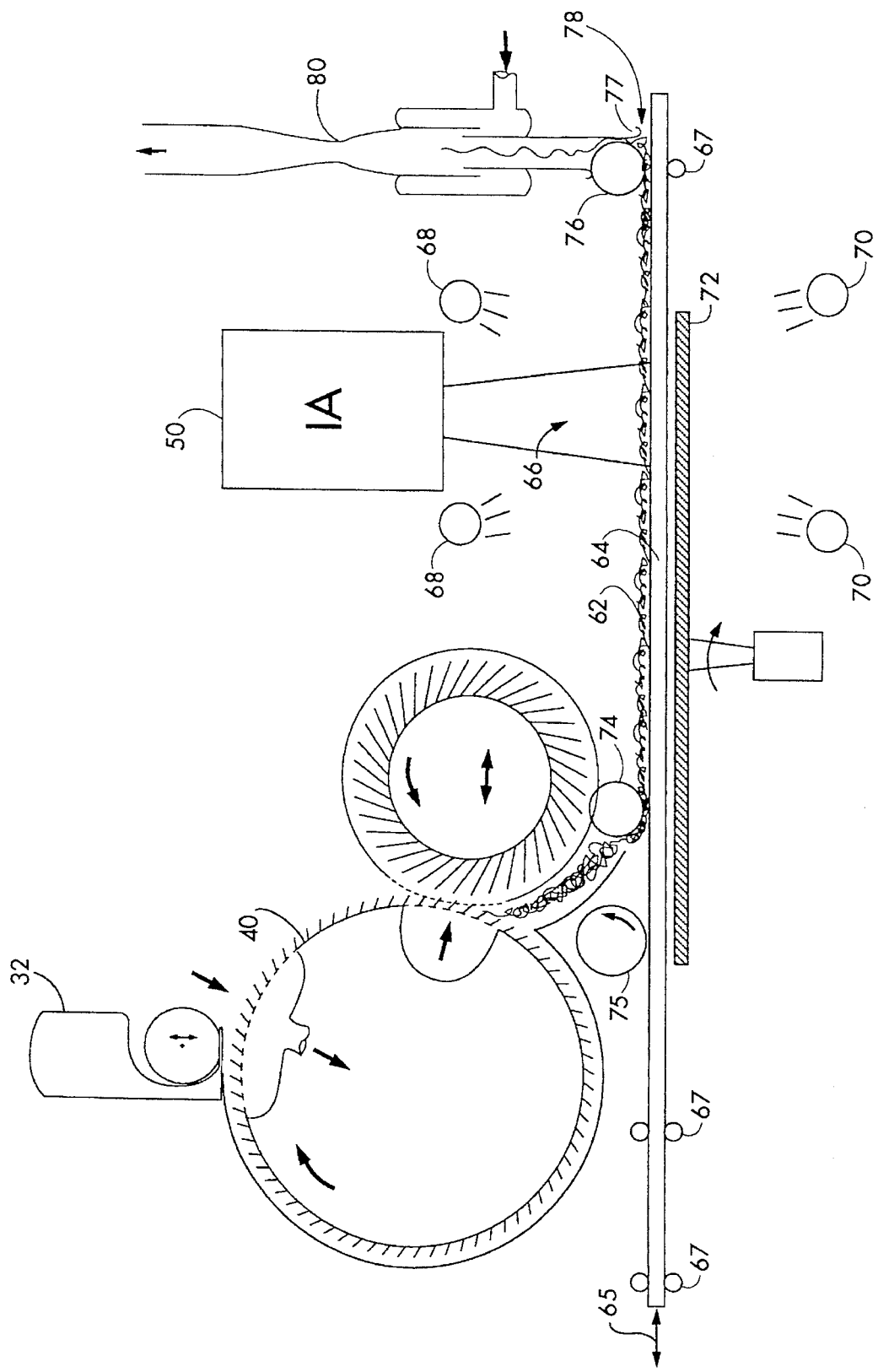
FIG. 4 is a drawing showing the sampler delivering fiber samples to a cylinder which, in turn, delivers the sample to a glass plate.

FIG. 4 reveals another embodiment utilizing substantially the same image analyzer measurement means 50. A thin web 62 is formed for presentation to the image analysis system 50. In this case the sample is acquired by needle sampler 32 and spread on the presentation cylinder 40 as before but in this case the thin web 62 is brushed off onto a glass plate 64 whose length is slightly greater than the circumference of the preparation cylinder 40. The plate 64 is mounted for left and right linear motion as indicated by arrows 65 and is driven by drive rolls 67. In this manner the density, orientation and other preparation and presentation features and effects on the sample by the cylinder 40 are retained, but a preferred viewing environment, 66 is provided. In this environment front lighting 68 and back lighting 70 may be used together or separately for preferred illumination. Background contrast and other elements are represented by the motor driven element carrier 72. The carrier 72 preferably provides a black background, but it also may represent white or other colors, a mirror surface, or no element at all, for the back lighting mode. A wide variety of backgrounds with front illumination could be chosen to enhance contrast or resolution or, in general, the ability to recognize entity patterns.

Upon completion of measurement the thin web sample 62 moves with the glass plate 64 under guide roll 76 and is removed by clean compressed air from purge source 77 and carried out by an air sweep 78 driven by coaxial adductor 80. The tested material is thus returned to the process as in FIG. 3. Cleaner wheel 75 removes residue and prepares the plate 64 for the next test.

Figure 5:
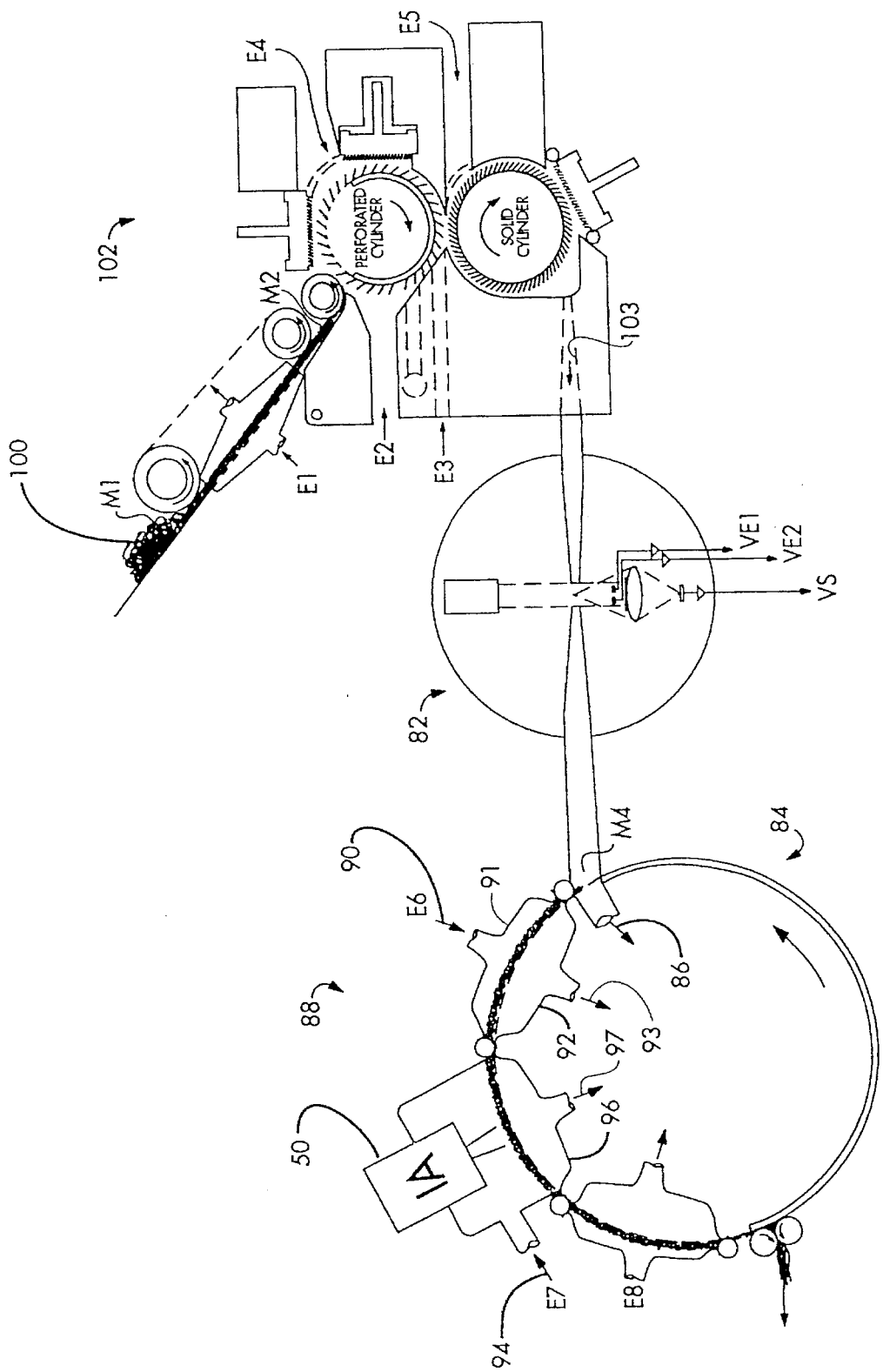
FIG. 5 illustrates another embodiment of the present invention in which textile fibers are processed by a fiber individualizer, transported through an individual fiber monitor, and deposited on a cylindrical screen for further monitoring.

FIG. 5 shows a fiber individualizing apparatus 102 supplying individual fibers and entities through a conduit to a sensing station 82 that in turn supplies the entities and fibers to a viewing station 88. The sample is individualized by apparatus 102. The individualized entities 103, after passing through electro-optical sensing station 82 (M3), are deposited on a rotating perforated drum 84. The deposition is aided by collection of the transport air by suction 86. At station 88 the image analysis system 50 is shown in similar function as in FIGS. 3 and 4. In this embodiment the sample has been conditioned with environmentally controlled gas 90, introduced at plenum 91 and discharged into a collection plenum 92 that is evacuated by suction 93. Also, the sample can be further conditioned by environmentally controlled air 94 which is similarly collected by plenum 96 and suction 97.

It is evident that the peripheral speed of perforated cylinder 84 can be adjusted in combination with the sample 100 feed rate into the fiber individualizer 102 so that essentially individual entities are presented for inspection both by the electro-optical sensor 82 and by the image analysis system 50. Slower speeds of the presentation cylinder 84 enable multiple entities to be deposited and inspected by the image analysis system 50 at station 88. It can be appreciated that the time stamping concept introduced in co-pending application Ser. No. 07/762,613, filed Sep. 19, 1991, may be applied between the signals from the electro-optical light scattering sensor 82 and the image analysis system 50 at station 88. That is, there is a fixed time delay between when the sample 100 is sensed at station 82 and at station 88. Thus, the measurements from stations 82 and 88 may be time correlated.

FIG. 6 reveals a most important embodiment for on-line process monitoring wherein image analysis means 50 inspect the thin web on a doffer cylinder 110 of a carding machine 112. Alternatively, image analysis means 50 inspect the web 120 as it exits the doff or crush rolls 122 and before it proceeds through a trumpet 125 and becomes a sliver 126. It will be readily understood that the entities, in terms of orientation and density, are essentially the same on the doffing cylinder 110 as in the web 120. It will also be appreciated that the relative advantages of inspecting the web in "free" space 124, where front lighting and back lighting are much more readily achieved, is preferable for the highest contrast and resolution. However, in some cases it is not feasible to measure the web at space 124 as indicated in FIG. 6. Further, in other cases the discrimination abilities of the image analysis system 50 are entirely adequate when examining the thin web as it is transported by the teeth on the doffer cylinder 110.

FIGS. 3, 4, 5, and 6 thus disclose means by which thin webs may be formed from samples of textile material for the preferred examination by image analysis means. The samples may be automatically acquired from an operating process, may be part of a test sample for a laboratory quality control instruments, or may be inherently found already as thin webs in carding machines or the like. All may be advantageously examined with our preferred image analysis means 50. We now turn to the image analysis subject and disclose the concept of spatial, spectral and temporal pattern recognition or filtering, SSTF.

IMAGE ACQUISITION SYSTEM

Referring now to FIG. 7, there is shown an overview of the optical imaging system 129 which includes first and second optical imaging units 130 and 132, which include CCD cameras. Each of the imaging units 130 and 132 is positioned to view at least a 0.5 meter wide section of a web 134 which is preferably a web of nonwoven textile fibers such as cotton. Preferably, the imaging units 130 and 132 are positioned to view approximately one-half of the web with an overlap 135 of approximately 0.01 meter. The purpose of two imaging units 130 and 132 is to provide 100% optical viewing of the web, but reduce the data rate by approximately one-half. That is, by analyzing the data from each optical unit 130 or 132 separately, the data rate is approximately one-half that which would be required if a single unit was viewing the entire web and the single camera was obtaining the same resolution as two imaging units.

The moving web 134 is illuminated by broad band radiation sources 136 and 138 which provide both visible and non-visible light including infrared. Source 136 illuminates the front of web 134 and source 138 illuminates the opposite side, the back side of web 134. With this illumination arrangement, the type of illumination impinging on the web 34 can be varied to provide information as to the amount of light transmitted through the web 134 from its back side or reflected from its front side or both.

The imaging units 130 and 132 and the illumination sources 136 and 138 are connected through data acquisition and control units 140 and 142 to an image processing and storage computer system 144. The optical imaging units 130 and 132 produce image signals that are transmitted through the units 140 and 142 to the system 144 for processing, and the computer system 144 also issues control commands through the units 140 and 142 to the illumination sources 136 and 138 and, thereby, controls the intensity and duration of the illumination on the web 134. The system 144 also includes an information link 146 that provides information and control to an excluder system that is hereinafter described.

OPERATION OF THE IMAGE ACQUISITION SYSTEM

Figure 9:
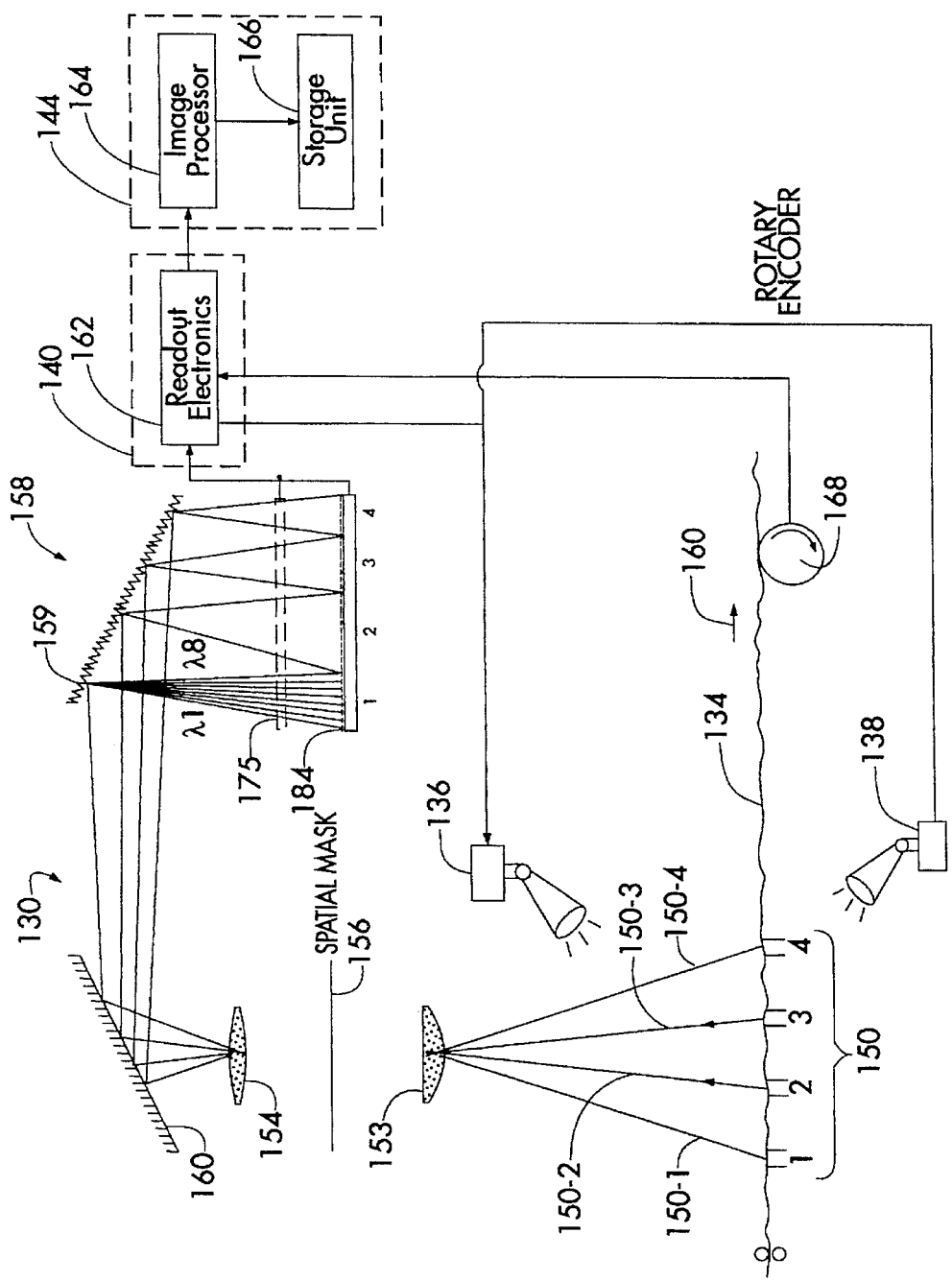
FIG. 9 is more detailed schematic diagram of the optical imaging system of FIG. 8.
Figure 10:
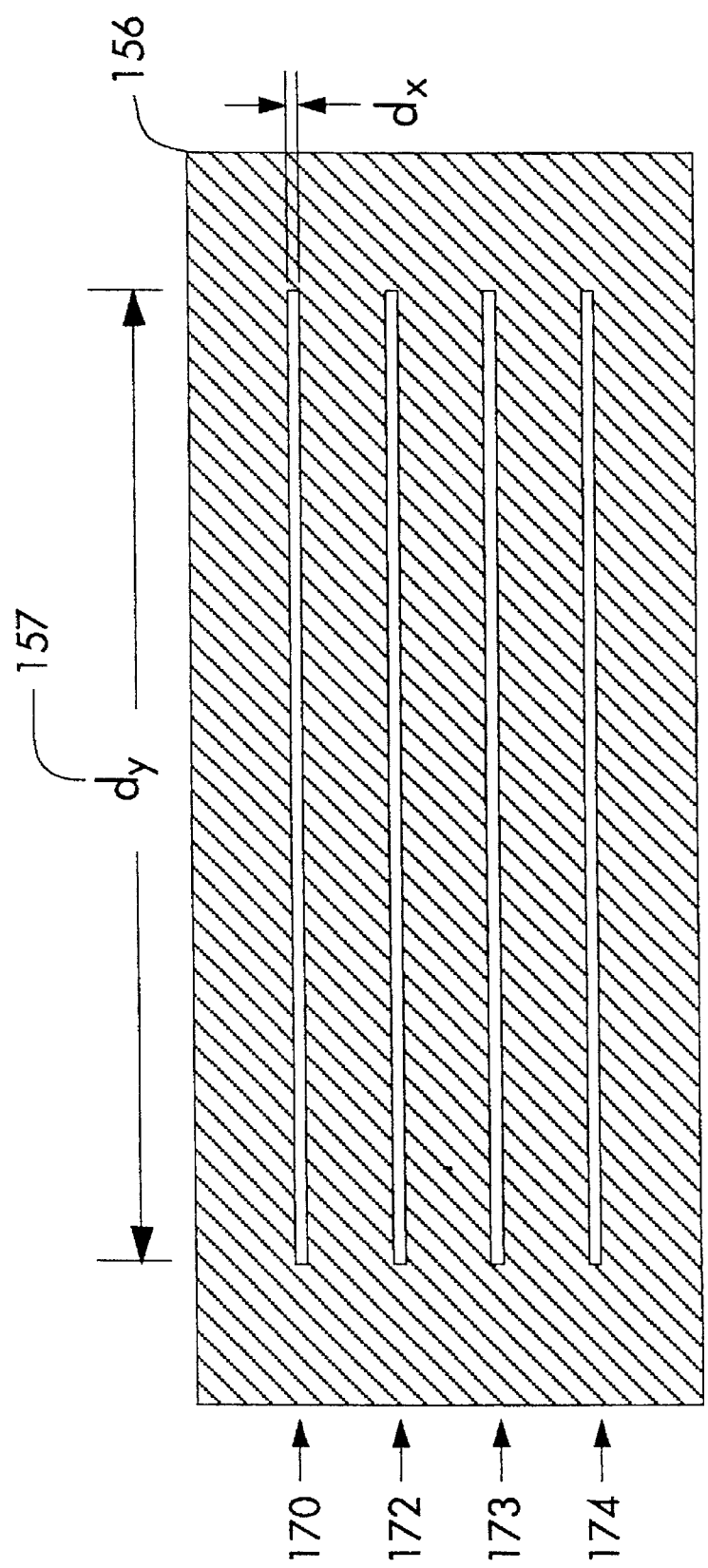
FIG. 10 is detailed view of a mask used in the optical imaging system of FIG. 8.
Figure 11:
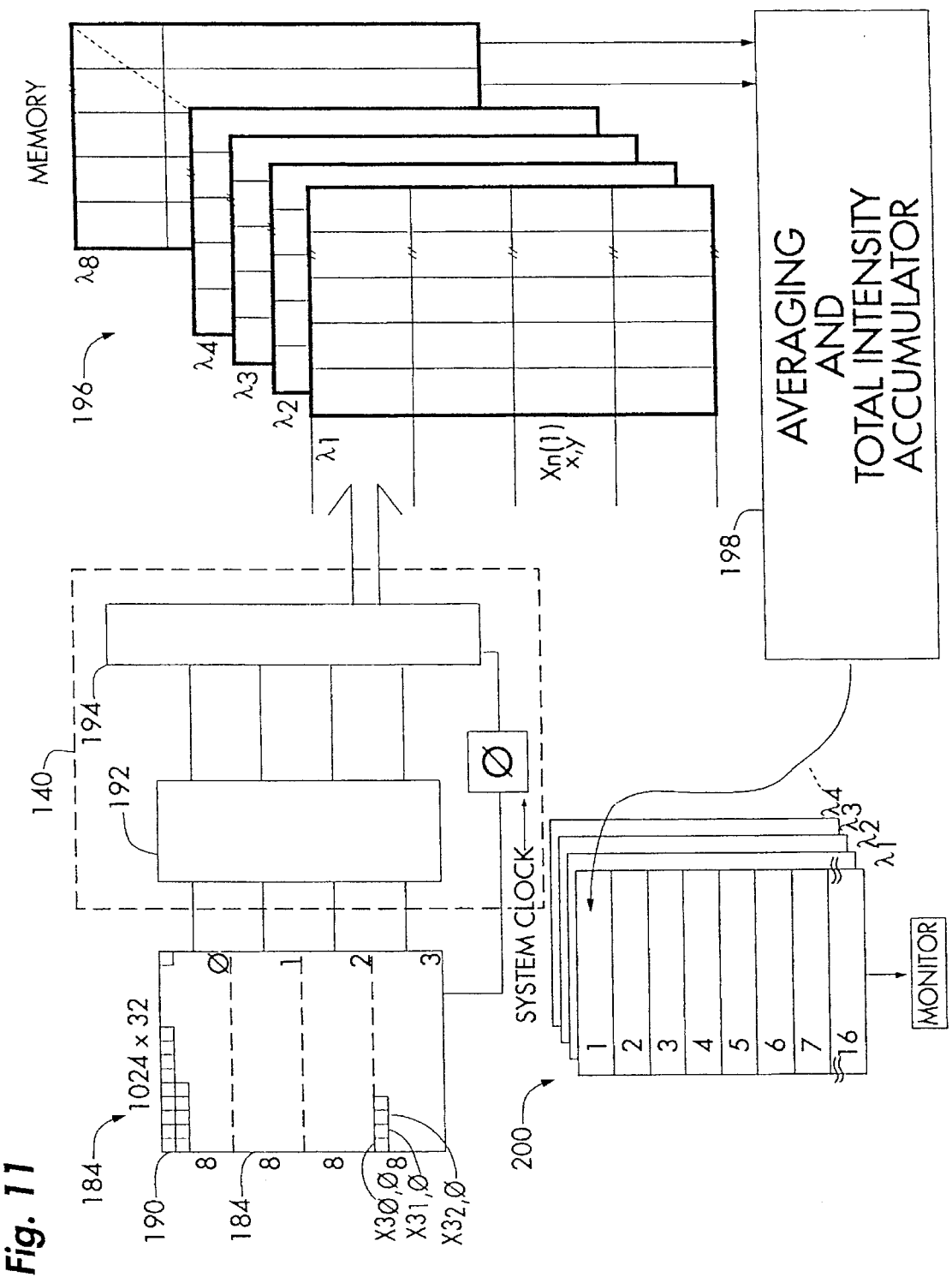
FIG. 11 is a schematic diagram illustrating how the CCD camera is read into memory and into an image buffer.

The detailed operation of each of the optical imaging units 130 and 132 is best understood by reference to FIGS. 8, 9 and 10. Referring to FIG. 8, there is shown a more detailed view of the optical imaging system 129 illustrating the operation of one imaging unit 130, it being understood that unit 132 functions in like manner. Referring to FIGS. 8 and 9, the optical unit 130 is configured to simultaneously view four stripes 150 across the web 134 that are labeled 1–4 on FIGS. 8 and 9. In the preferred embodiment, each of the stripes 150 has a width of 0.5 millimeters and extends in a traverse direction (i.e., perpendicularly) across the web 134 for a distance of approximately 0.510 meters. Since two optical imaging units 130 and 132 are used to view the entire web, the stripes 150 may be thought of actually extending continuously across the web. The leading edges of the four stripes 150 numbered 1–4 are separated from each other by a distance of precisely 4.0 millimeters where the leading edges are those edges of the stripes closest to the direction in which the web 134 moves. Thus, the spacing, edge to edge, between the four stripes 150 is 3.5 millimeters.

The optical imaging unit 130 includes a pair of lenses 153 and 154 and a spatial mask 156. The purpose of the lenses 153 and 154 is to focus an image of the web 134 unto a CCD camera and grating assembly 158 after reflection from mirror 160. The function of the spatial mask 156 is to restrict the view of the CCD and grating assembly 158 to the four stripes 150. Since the web 134 is moving in the direction indicated by arrow 160, it will be appreciated that the CCD and grating assembly 158 is viewing the web four separate times. That is, all of the web 134 will pass through each of the four stripes 150. Therefore, that portion of the web 134 that is first viewed in the first of the stripes 150 will be viewed a second time in the second stripe 150, a third time in the third stripe 150, and a fourth time in the fourth stripe 150. As described in greater detail hereinafter, this redundancy is provided for the purpose of increasing accuracy and/or increasing the amount of information obtained.

The signal from the CCD and grating assembly 158 is transmitted to readout electronics 162 which is a part of the acquisition and control unit 140. The readout electronics 162 provides an output to an image processor 164 whose output is applied to a display and storage unit 166, both of which are part of the image processing and storage computer system 144.

The speed of the web 134 is constantly monitored by a speed detector, such as a rotary encoder 168, that provides speed information through readout electronics 162 to the computer system 144. This speed information is important so that the system can take advantage of the redundancy provided by the four stripes 150 and so that items of interest, such as trash, detected by the assembly 148 may be tracked as to position downstream in the web and excluded.

Referring now to FIG. 10, a detailed view of the mask 156 is shown. The mask 156 includes slits 170, 172, 173, and 174 that restrict the viewing angle of the CCD and grating assembly 158 to the four stripes 150. Thus, the slits 170, 172, 173, and 174 control the size and shape of the stripes 150. Since it is desired to provide stripes having a width ($W_1$) of 0.5 millimeters, the width ($d_x$) is determined by the product of the desired image width, 0.5 millimeters, and the magnification (M) of the first optical element 152. The width of the mask ($d_y$) is determined by the product of the magnification of the lens 152 and the width ($W_2$) of the web that is desired to be inspected (approximately 0.512 meters). Thus, for an optical element 152 with a focal length (F) of 60 millimeters located a distance ($d_0$) of 1 millimeter away, one would calculate as follows:

$$d_i = \frac{(f)(d_0)}{(d_0 - f)}$$

$$d_i = \frac{(1)(.06)}{(1 - .06)}$$

$$= 63.83 \text{ mm}$$

$$M = \frac{d_i}{d_0} = \frac{63.83 \text{ mm}}{1000 \text{ mm}} = 63.8 \times 10^{-3} \text{ mm}$$

$$d_x = (W_1)(M) = (.5 \text{ mm})(63.8 \times 10 - 3 \text{ mm}) = 32 \text{ µm and}$$

$$d_y = (W_2)(M) = (.512 \text{ m})(63.8 \times 10 - 6 \text{ m}) = 32 \text{ mm}.$$

The mask 156 can be constructed of precision cut metal film or a chrome ruling on a glass substrate.

Referring now to FIG. 9, there is shown a somewhat diagrammatic cross-sectional view of the CCD array and grating assembly 158. Light entering the assembly 158 passes through an electronic shutter 175 controlled by computer system 144. Light first impinges upon a diffraction grating 159. After passing through the shutter 175, the light impinges upon a CCD array 184. The diffraction grating 159 disperses the incoming light into eight spectral channels, and the grating is oriented so that dispersion occurs in a direction corresponding to the movement direction of the web. Thus, the dispersion occurs in a direction perpendicular to the slits 170, 172, 173 and 174 (FIG. 10) and perpendicular to the four stripes 150 (FIG. 9). The diffraction grating is designed and dimensioned so that it spreads eight spectral channels over an area of the CCD corresponding to 4 millimeters on the web (eight stripes on the web). Thus, instead of forming one image of each of the stripes 150 on the array 184, the system focusses eight side-by-side images of each of the stripes 150 on the array 184. It will now be appreciated that the size of the four stripes 150 and the spacing between the stripes 150 was chosen to allow for precisely eight images of each stripe on the CCD array 184 without allowing any overlap. Since the diffraction grating separates the light into spectral channels, each of the stripe images formed on the array 184 will provide different color information for each of the stripes 150. This design leads to a simple, compact design for observing color information in the visible wavelengths using a CCD array 184 that measures only the intensity of the light striking it.

In the above description, particularly with reference to FIG. 9, optical imaging unit 130 has been described along with the acquisition and control unit 140. It will be appreciated that the optical imaging unit 132 and 142 are substantially identical to units 130 and 140, respectively, and FIG. 9 will be understood to describe and represent both imaging units 130 and 132 and both acquisition and control units 140 and 142.

The operation of the system 129 shown in FIG. 8 may be better understood by reference to the electronic and digital processing that is illustrated in FIGS. 11–14. The CCD array 184 consists of 1024 by 32 image pixels 190 arranged so that the 32 pixel dimension lies parallel to the movement of the image of web 134 on the array 184, and the rows of 1024 pixels 190 are oriented to be perpendicular across the image of the web 134 appearing on the array 184. The array 184 is preferably read four pixels at a time by an A/D convertor 192 where the voltage sensed by each pixel 190 is converted to a digital number which is output through the DEMUX 194 to digital memory 196. The memory is read by an averaging and total intensity accumulator 198 and its output is applied to an image buffer 200. The function of the accumulator 198 is to average four rows of 1024 pixel output from the array 184 to produce each row of the image placed in the image buffer 200. The averaging process may best be understood by again referencing FIG. 9 and considering a single one-half millimeter segment of the web 134 as it passes across the stripes 150. Consider first that this hypothetical segment first appears over the first stripe 150. The electronic shutter 175 will expose the CCD 184 and this hypothetical segment of the web will be viewed for the first time. The segment will then move from the first stripe 150 to the second stripe 150. The image processor 144 receives speed information from the encoder 168 and causes the shutter 175 to open each time the web moves one-half millimeter. Thus, the hypothetical segment will be positioned over the second stripe 150 when the shutter 175 opens for the ninth time and the segment will be viewed for a second time by the CCD array 184. Likewise, on the seventeenth exposure of shutter 175, the segment will be over stripe 3; on the twenty-fifth exposure of shutter 175, the hypothetical segment will be over stripe 4 and, thus, it will be viewed for the third and fourth times. From the above explanation, it will be appreciated that each segment of the web will have the same hypothetical journey as described above and will be viewed four times. Thus, by averaging the first, ninth, seventeenth and twenty-fifth viewing of each 0.5 mm segment, an average measurement for each segment is obtained.

Figures 12A, 12B, 12C, 12D:
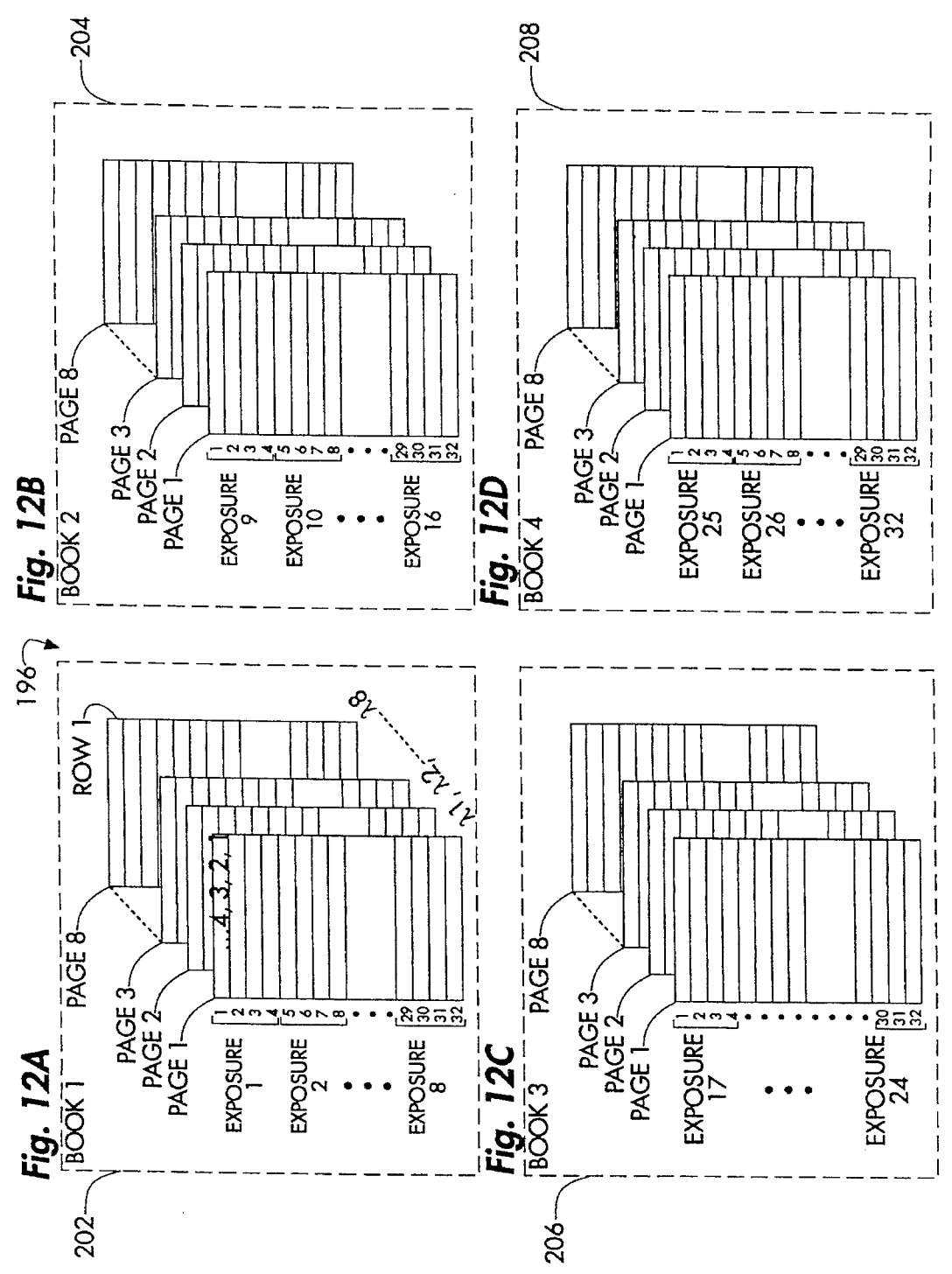
Figure 13:
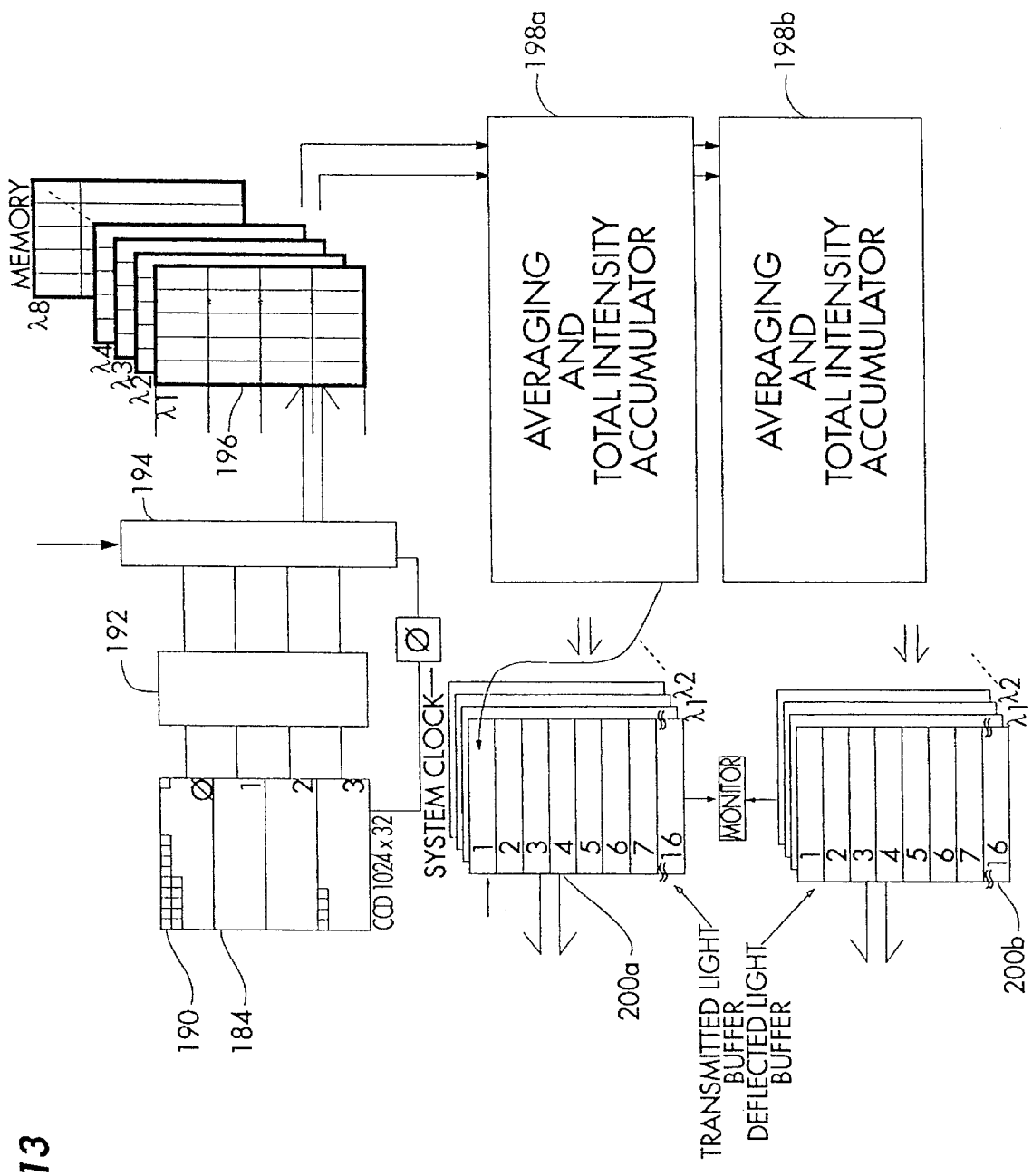
FIG. 13 illustrates an alternate system for reading the CCD camera and storing images in memory.

Referring now to FIG. 12, the control of the memory 196 may be visualized. The memory 196 is divided into four books, books one through four, which are identified by characters 202, 204, 206 and 208. Referring to FIGS. 12 and 13, the acquisition of data is explained as follows. Upon the receipt of a correct position indication from the rotary encoder 168 (FIG. 9), the shutter 175 (FIG. 11) opens for approximately 0.0001 second to expose the CCD array 184. The process of image acquisition begins by reading the first 1024 pixel line of the CCD array 184, four pixels at a time, and storing it in the rightmost 1024 locations of the first row of the first page of the first book. The next 1024 pixel line is read from the array 184 and is stored in book one, page two, row one, because it represents the same spatial information as the first line, but at a different spectral wavelength. Each book contains eight pages and the first eight lines of the CCD array 184 are read into the first rows of the eight pages of book one. The next eight lines of the CCD array are stored in the second row of the eight pages of book one. The next eight lines of the CCD array 184 (lines 16–24) are stored in row three of pages 1–8 of book one, and the final eight lines of the CCD array 184 are stored in row four of the eight pages of book one.

The CCD has now been fully read, and it is cleared and the processor 144 waits until the encoder 168 indicates that the web 134 has moved forward 0.5 millimeters. At that point, the shutter 175 will expose again and create exposure number two. Exposure number two is stored in book one, rows 5–8, of pages 1–8 in the manner described above. Likewise, subsequent exposures are stored in book one until exposure eight is stored in rows 29–32 of pages 1–8 of book one. On the ninth exposure, book two is begun as indicated by character 204 in FIG. 17. Book two will contain exposures 9–16. Likewise, books three and four are created for storing exposures 17–24 and exposures 25–32, respectively. From the above discussion it will be appreciated that book one contains the oldest exposures and book four contains the most recent exposures.

It will further be appreciated that row one of each of the pages in book one should correspond to the same web segment image as row two of each of the pages of book two, as row three of each of the pages of book three, and as row four of each of the pages of book four. Thus, to produce row one of the first page in the image buffer 200, the accumulator 198 averages book one page one row one+book two page one row two+book three page one row three+book four page one row four. The accumulator 198 produces row one of pages 2–8 in the image memory buffer from pages 2–8 of books 1–4 in the same manner as described above.

To produce row two of page one in the image buffer 200, the accumulator 198 uses data obtained from exposures 2, 10, 18, and 26. Row two of image buffer 200 is obtained by averaging book one page one row five+book two page one row six+ book three page one row seven+book four page one row eight. Likewise, each succeeding exposure is used to create the first eight rows in the eight pages of the image buffer 200. As another example, to produce row ,eight of the image buffer 200, the accumulator 198 adds book one row twenty-nine+book two row thirty+ book three row thirty-one+ book four row thirty-two. After the eighth row of image buffer 200 has been calculated, books two, three and four are redesignated as books one, two and three, respectively. Then, a new book four is created using the next eight exposures from the CCD 184, and the next eight rows for each of the eight pages of the image buffer 200 are calculated in the same manner as the first eight rows were calculated. This process continues indefinitely so that the image buffer 200 is a scrolling image buffer and always contains sixteen rows of image information on all eight pages. From the above description, it will be appreciated that the image buffer always contains eight images, which have been referred to as "pages", of sixteen rows each of the web 134. Each of the eight images (pages) differs from the other in image buffer 200 based on frequency (color). That is, each image represents a particular spectral range. If the web is producing an image in that particular spectral range, then such image will appear on the page of image buffer 200 containing that particular spectral range.

The output of the image buffer 200 is further analyzed as described in greater detail hereafter following a description of an alternate embodiment shown in FIG. 13 in which the accumulator 198 has been divided into two accumulators 198A and 198B, and the image buffer 200 has been divided into two buffers 200A and 200B. It will be understood that FIG. 13 is symbolically representing these elements and it is not necessary to actually physically separate the accumulators or the image buffers, but it is helpful to the explanation of the operation to so separate them.

The embodiment shown in FIG. 13 illustrates another way to take advantage of the redundancy that is built into the system 129. It will be recalled that each segment of the web 134 is viewed or imaged four times by the CCD 184. In the embodiment described above, these four redundant images were averaged to produce a single image. However, in the embodiment shown in FIG. 14, the redundancy is used in a different way. To utilize this embodiment, the illumination of the web 134 is changed after every sixteen exposures. For example, during the first sixteen exposures, the light source 138 is turned on to illuminate the web 134 from the back side of the web so that only light which transmits through the web is received by the detector 184. On the second sixteen exposures (exposure 17–32) source 138 is turned off and source 136 is turned on so that only light reflected from the web is received by the array 184. Thereafter, the sources 138 and 136 are alternately turned on and off every sixteen exposures so that the web 134 is illuminated only from one side at a time. The accumulator 198A produces the image buffer 200A in book form in the manner described above, except that accumulator 198A receives data only from the first set of sixteen exposures plus every odd set of sixteen exposures thereafter when the source 138 is on. The accumulator 198 produces the image books in buffer 200B based only on even sets of sixteen exposures when source 136 is on and source 138 is off. Thus, image buffer 200A contains a transmitted light image and buffer 200B contains a reflected light image. Each of these images is actually eight images contained on eight separate pages in the manner described previously.

Another method for operating accumulators 198A and 198B is to change to the illumination after every eight exposures so that source 138 is on during exposures 1–8 and exposures 17–24, while source 136 is on during exposures 9–16 and 25–32. In such case, the accumulator 198A would produce information for the image buffer 200A only from odd numbered sets of eight exposures, and 198B would produce data for image buffer 200B only from even numbered sets of eight exposures.

Since there is a quadruple redundancy provided by the system shown in FIG. 9, if desired, all true redundancy may be eliminated and the web 134 may be observed under four different light conditions as it passes stripes 150. For example, the mat could be exposed to four different light conditions such that a different type of illumination is present each time a segment of the mat passes beneath one of the stripes 150. For example, the mat 134 could be illuminated with the color red for the first eight exposures, the color green for the second eight exposures, the color yellow for the third eight exposures and the color blue for the fourth eight exposures. On the fifth set of eight exposures, the light conditions would be cycled again in the same order as before for each set of eight exposures. In this manner, each segment of the mat 134 will be exposed to four different light conditions as it passed through stripes 150, and different portions of the mat 134 will be exposed to the various light conditions at differing locations. For example, one portion of the mat may be exposed to red at stripe one, whereas another portion of the mat will be exposed to red at stripe two. However, all segments of the mat will be exposed to all four light conditions, just at different positions. In this embodiment, it would be preferred to use four accumulators, such as accumulators 198A and 198B, each accumulator being programmed to .accept data only when a certain light condition is illuminating the mat 134. In such case, each accumulator would be responsive to data from every fourth set of eight exposures.

By the examples given above, it is meant to illustrate that the optical system of FIG. 9 can be constructed with a desired amount of redundancy by changing the number of stripes 150. This redundancy can be used to reduce the signal to noise ratio by exposing the mat 134 identically as the mat passes under each of the stripes 150 and then averaging the results. Or one may use the redundancy to expose the mat to differing light conditions, such as different wavelengths or directions or type of light, and thereby acquire more information about the web 134.

Referring again to FIGS. 11 and 13, it will be recalled that the array 184 includes lines of 1024 pixels and each pixel observes a 0.5 mm×0.5 mm area of the web 134. Since the overall width of the web 134 is 1 meter, the two optical imaging units 130 and 132 may be set to overlap anywhere from 0 to 24 pixels. In the preferred embodiment, the units 130 and 132 are set to overlap by 20 pixels or 0.01 meters and, thus, each camera also has a viewing angle that overhangs the web on the outer edges by a distance of 4 pixels or 2 millimeters. The overlapping regions of the optical imaging units 130 and 132 are used to align the units 130 and 132 so that they are viewing precisely the same portion of the web 134 in the overlap region. Thus, the overlap insures full viewing of the web 134 and it facilitates alignment of the units 130 and 132. Also, it will be appreciated that a single optical imaging unit may be substituted for the units 130 and 132 by either reducing the desired resolution or by using a higher resolution CCD array 184.

IDENTIFICATION OF ENTITIES

Figure 14:
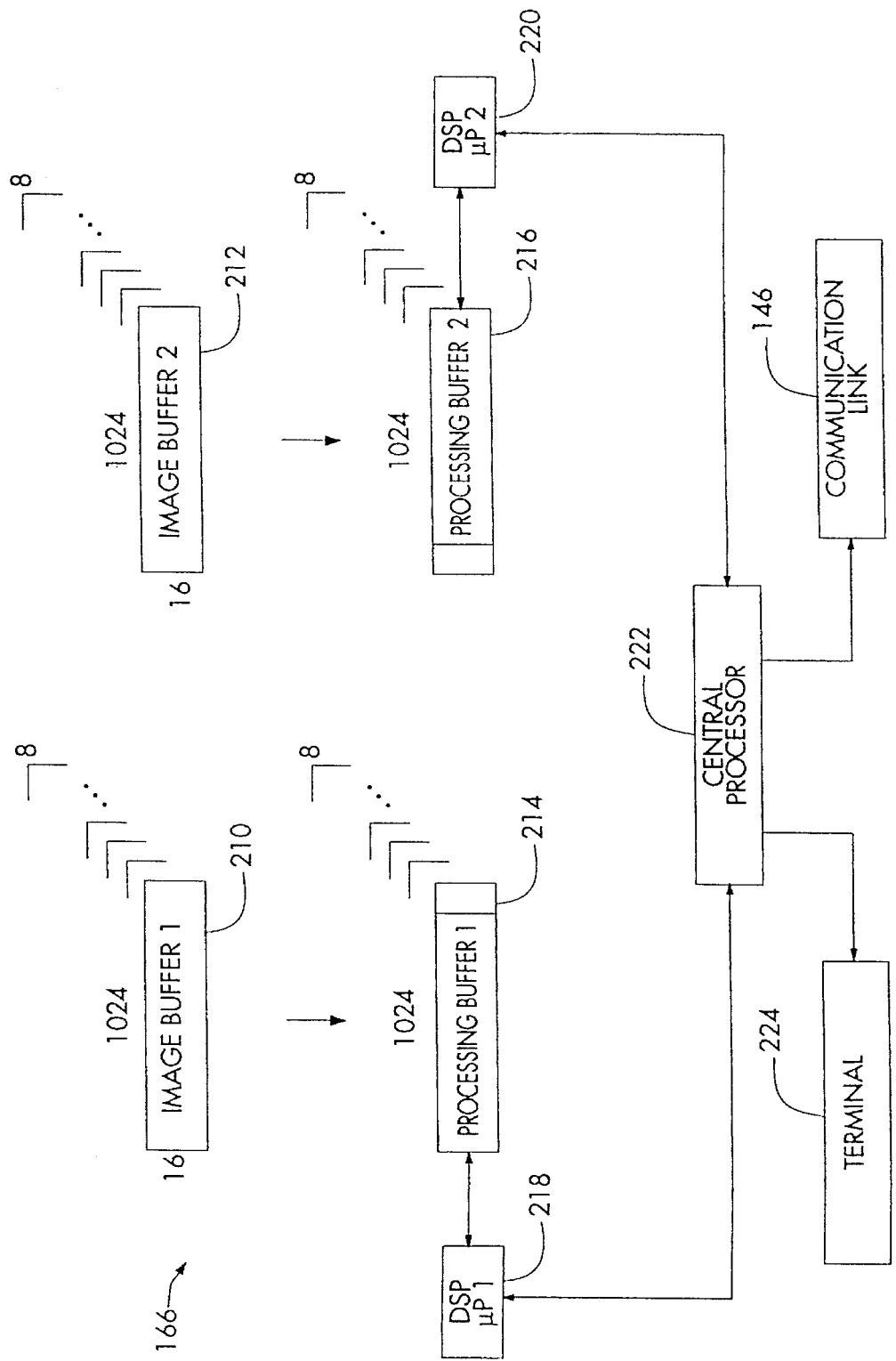
FIG. 14 is an overall block diagram of the processing system used to process the images produced by the optical imaging system.

Referring now to FIG. 14 a block diagram of the display and storage system 166 is shown. In this figure, two image buffers 210 and 212 are shown and each of these buffers is identical to buffer 200 shown in FIG. 11. Thus, the buffers 210 and 212 each contain eight images in eight memory locations which may be regarded as pages. Each of the pages is a 16 by 1024 array of data. The data of the image buffers 210 and 212 are read into processing buffers 214 and 216, respectively. Two digital signal processors (DSP) 218 and 220 are provided for operating upon the data in buffers 214 and 216, and each of the two DSP processors 218 and 220 is under the control of a central processor 222. The processor 222 is also connected to a conventional terminal 224 and to a communication link 146.

Figure 17A:
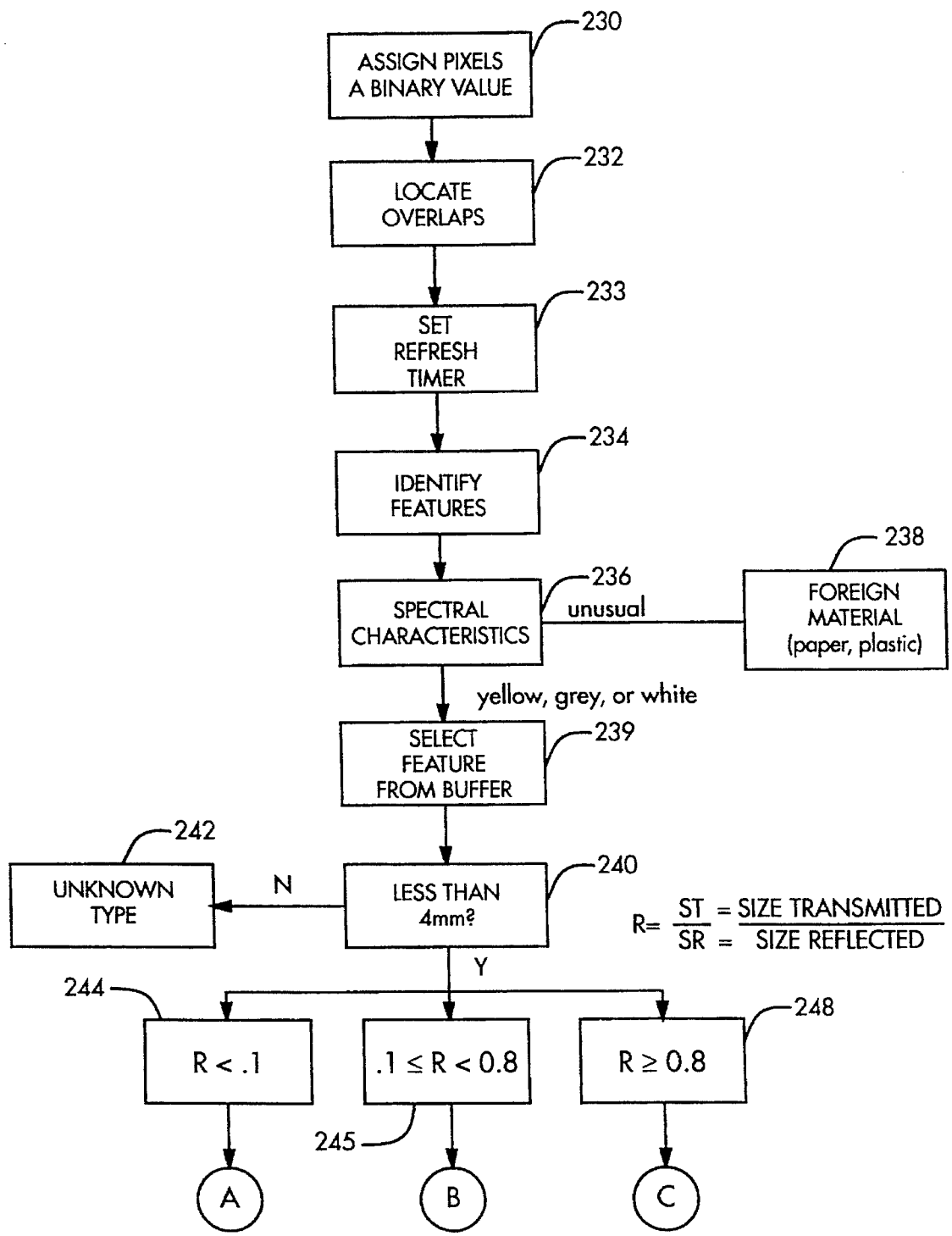
FIGS. 17A and 17B constitute a flow chart illustrating he operation of a computer program illustrating one method for using the optical system of the present invention for distinguishing between different entities in a textile web.
Figure 17B:
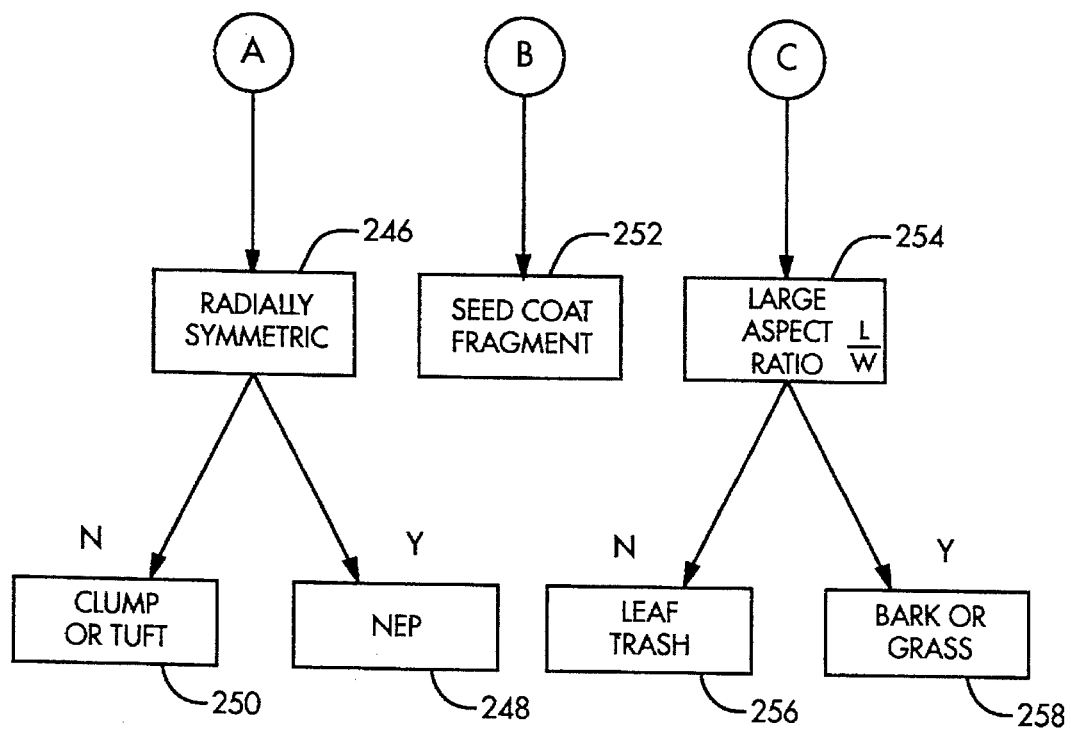
Figure 19:
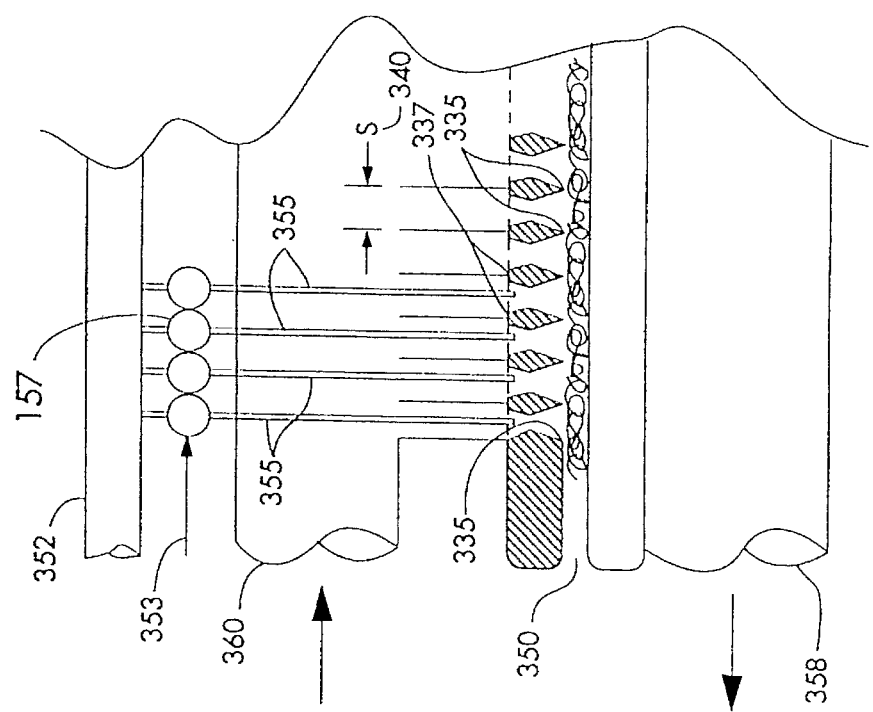
FIG. 19 shows a cross-sectional view of the excluder taken through section lines 19—19 shown in FIG. 18.

The raw data stored in the processing buffers 214 and 216 represents a multiplicity of features of the web 134. The DSP's 218 and 220 and the central processor 222 are programmed to use the spectral and spatial information contained in the images to locate entities of interest and classify or identify them. For example, in the preferred embodiment, the system 166 is programmed to locate trash and neps in a non-woven web of fiber 134. Referring to FIG. 17A, the first step 230 in the program is to assign each pixel in the processing buffers 214 and 216 a binary value, 1 or 0, depending on its intensity value. For present purposes, we define any pixel having a value 1 (on) to be a feature, and any pixel with a value of 0 (off) to be background. For image information that was received in the transmitted light mode, objects of interest attenuate light so the program assigns a value of 1 to any pixel that is less than 30% of the background values for all of the pixels. For image information that was obtained in the reflective light mode, we are interested in pixels that have a value that is 30% above the background value and they are assigned a value of 1 and the remaining pixels are assigned a value of 0. This assignment of a binary value is performed for all of the images in the eight pages of the buffers 214 and 216. By assigning the binary values in the manner described above, the same feature recognition techniques and sizing algorithms may be used to operate on images produced by either transmitted or reflected light.

As indicated by step 232 in the flow chart following the conversion to a binary image, the image buffer is screened by checking the upper pixel row for feature overlapping. This can be accomplished by checking each pixel surrounding an upper row of pixels. If all five of the adjacent pixels are value 1, then the feature is considered to be an overlap. The number of rows occupied by that feature is then determined and that number is provided to the control circuitry to advance the refresh time by that number of rows. In this manner, the image buffer refresh time is controlled so that the images provided to the processing buffers 214 and 216 do not overlap the edges. In an alternate embodiment, rather than control the refresh timing of the image buffers to avoid overlaps, the processor identifies features of interest that lie on the last row (trailing edge) of the buffers 214 and 216. These identified features on a boundary are saved in a separate memory represented by the DSP's 218 and 220. Then, when the processing buffers 214 and 216 are refreshed, the first row (leading edge) of each of the buffers 214 and 216 is analyzed to locate the remaining portion of the saved feature that overlapped the boundary between the two pages in buffers 214 and 216. In this manner, the DSP's 218 and 220 reconstruct a single feature (particle image) from two features that overlapped a boundary.

Figure 16C:
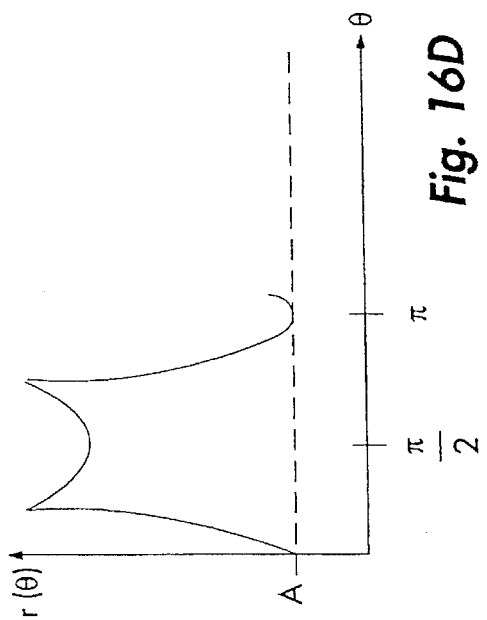
FIGS. 16A and 16C represent possible geometric shapes of entities and FIGS. 16B and 16D represent feature signatures of the entities shown in FIGS. 16A and 16C, respectively, where the signatures are generated by rotating a radius about the centroid of the geometric shape and graphing the length of the radius against its angular position.
Figure 16D:
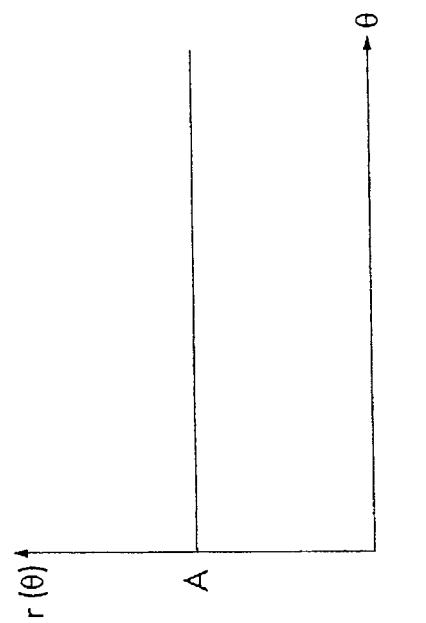
Figure 16A:
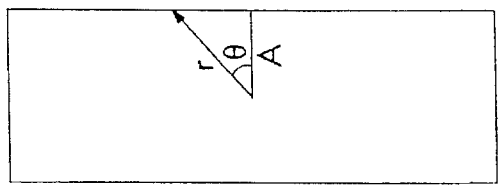

After overlaps have been identified and compensated for, features are identified at step 234. Features are defined as two adjacent pixels with a value of 1. Adjacency can be horizontal, vertical or diagonal, and the total size of the particle is calculated by counting all adjacent pixels. The boundaries of these features are then determined, such as by tracing techniques, high pass filtering or derivative calculations. Once the features have been located and the boundaries have been determined, the features are further identified as to shape. For example, shape is determined by approximating the boundary of a feature with a polygon using well known merging and splitting techniques. This technique works well because we expect relatively simple geometric shapes for most trash in cotton fibers and are primarily interested in the aspect ratio of the feature. An alternate method for determining the shape of a feature is to define a one-dimensional signature of the particle boundary. In accordance with this method, the distance from the centroid of the feature to the boundary of the feature is recorded as a function of the angle of the centroid. In FIG. 16A, a circular feature is illustrated with its corresponding signature produced by rotating a centroid shown in FIG. 16B. Compare the signature shown in 16B to the signature produced by rotating a centroid through a rectangle such as shown in 16C to produce the signature shown in 16D. This method is particularly suited to recognizing particles with a high degree of radial symmetry. Another advantage of this approach is that the features can be represented in one dimension, thereby saving storage space and processing time.

After the features have been located and information has been obtained as to their size and shape, as indicated by step 236, the features are classified beginning with features with unusual spectral characteristics. Cotton color ranges from white to a very faint yellow in appearance, and any material which exhibits strong spectral responses other than yellow or white must be regarded as composed of foreign material for removal. For example, a nep containing sugar will exhibit a strong spectral response in the near infrared spectrum. Thus, any feature that has a strong response in the near infrared spectrum should be tagged as foreign material and removed as hereinafter described. The step 238 in the flow chart FIG. 17A indicates immediate identification of foreign material based on spectral characteristics of a feature.

Next, features are selected one at a time from the reflected light buffer as indicated at step 239. If the feature is greater than 4 millimeters in diameter in any direction, for this particular application, it is regarded as an unknown foreign particle because most particles of interest such as trash, neps and seed coat fragments are smaller than 4 millimeters.

Figure 16B:
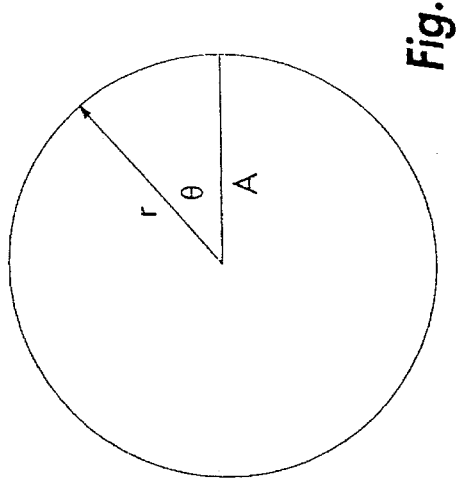

Next, the size of the same feature when illuminated with transmitted light and a ratio is calculated. That is the size of the particle as observed in transmitted light is divided by the size of the particle as observed in reflected light. Since cotton is rather translucent, especially in a thin web, cotton itself is primarily observed by reflected light, as opposed to transmitted light. In contrast, opaque contaminants such as trash, grass and bark are revealed with high contrast under transmitted illumination, because they block substantially all of the light. Conversely, tight entanglements and clumps of fibers known as neps are best revealed in reflected light. Seed coat fragments which consist of both a translucent fiber mass and an opaque seed coat core are determined by comparing the response for both transmitted and reflected illumination. As shown in the flow chart FIG. 17A at step 244, if the aforementioned ratio is less than 0.1, the feature is evaluated for radial symmetry at step 245. If the feature has radial symmetry, such as shown in FIGS. 16A AND 16B, as indicated at step 248, it is identified as a nep. Otherwise it is identified as a clump or tuft as indicated of FIG. 17B. Referring to step 245, if the ratio falls between 0.1 and 0.8, it is immediately identified as a seed coat fragment as indicated at step 252. Finally, if the ratio is greater than 0.8 the program analyzes the aspect ratio as indicated at step 254. If the aspect ratio is small, such as less than 2, the particle is identified as leaf trash as indicated by step 256. On the other hand, if the aspect ratio is large, such as greater than 4, the trash is classified as bark or grass as indicated by step 258. The identification and classification of particles in the cotton web, such as the web 134 shown in FIG. 8, is useful for making decisions concerning the processing of the cotton both upstream and downstream from the point at which the cotton is observed. For example, if a very trashy cotton web is observed, the operator may choose to begin with cleaner cotton or increase the cleaning efficiency of upstream machines. If a particular type of trash is observed, it may indicate a particular type of problem upstream. For example, if odd color conditions are observed, it may indicate that a portion of a dyed rag has been introduced into the cotton upstream, and this event could ruin a great amount of end product.

Likewise, the identification and classification of particles in a cotton web provides useful information for downstream processing. For example, sugary neps, which would be indicated by a strong image in the near infrared region, interfere significantly with processing machinery and degrade the end product. Thus, in downstream processing, the elimination of the sugary neps could receive a high priority. In some applications, small leafy trash may present no problem, while grass fragments would be of concern. In such case, the downstream processing would emphasize the elimination of the detected grass and, perhaps, ignore the leafy trash.

EXCLUSION OF ENTITIES

Figure 18:
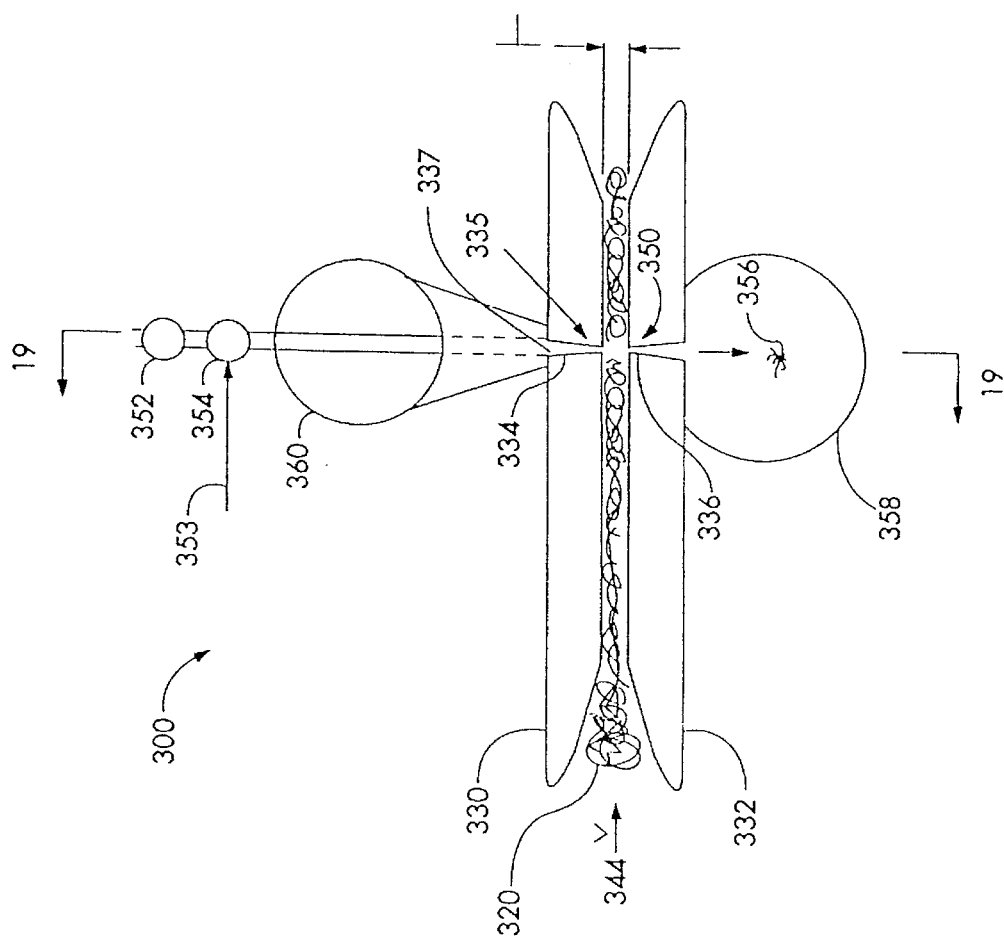
FIG. 18 shows an end cross-sectional view of a preferred excluder (ejector) of the present invention.
Figure 21:
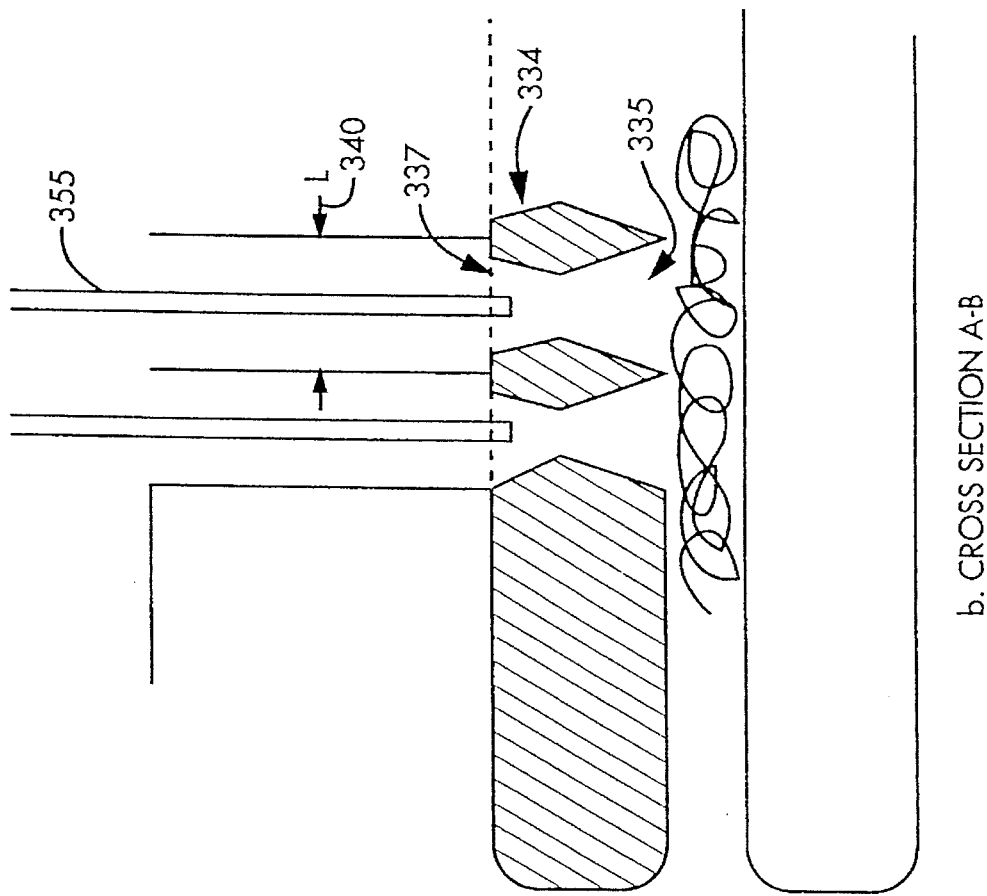
FIGS. 20 and 21 are enlarged views of the excluder corresponding to FIGS. 18 and 19, respectively.
Figure 20:
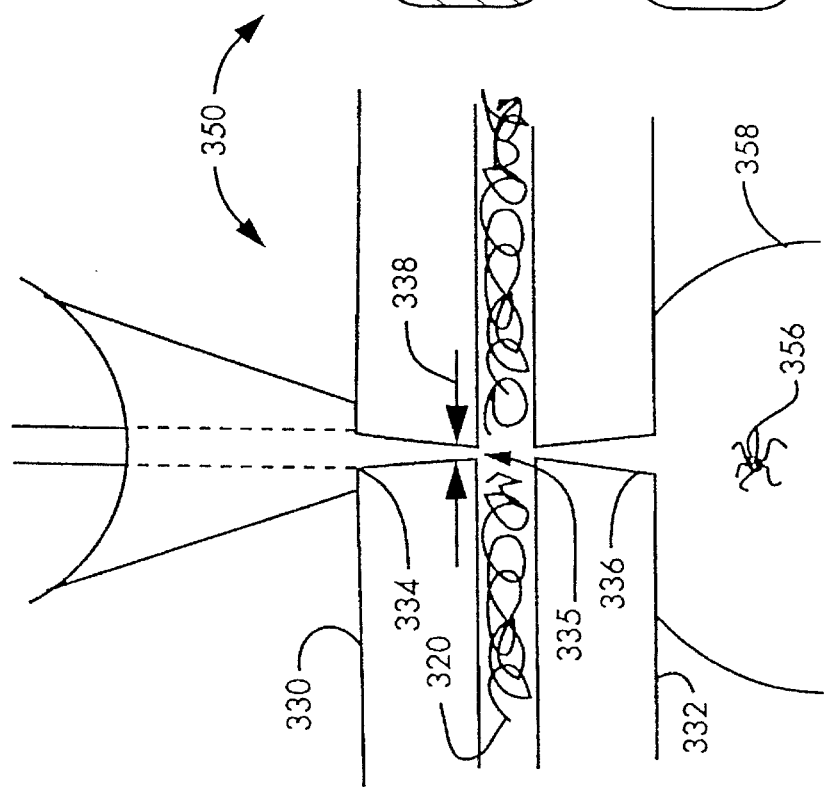
Figure 22:
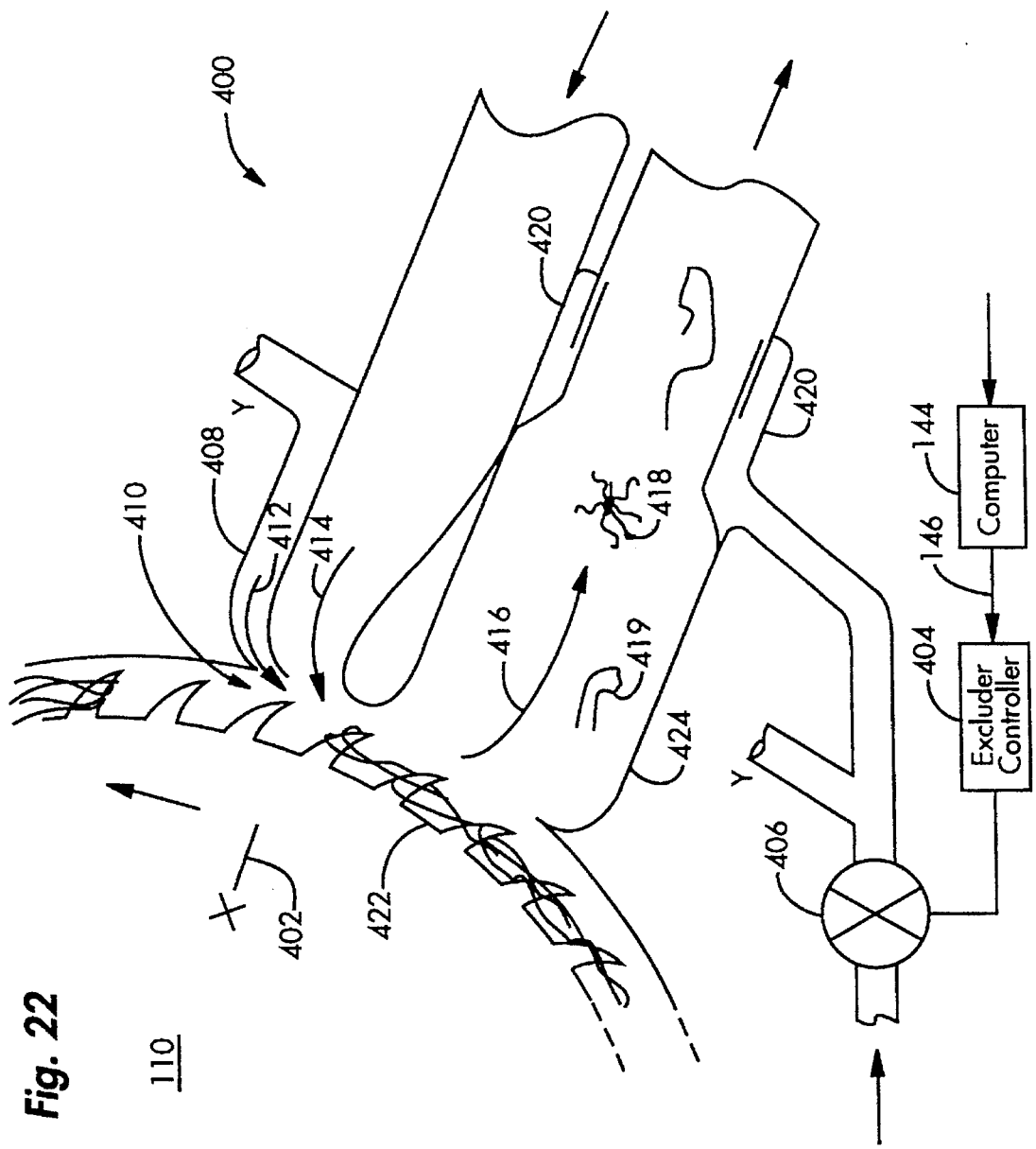
FIG. 22 is a cross-sectional view illustrating an ejector system of the present invention implemented in conjunction with a clothed cylinder such as a doffer cylinder.

Having described the above apparatus and method for finding and identifying trash in a cotton web, excluding undesirable entities from the thin web is now discussed. By means of the apparatus and method described above, entities are found and then identified in a prioritized classification as worthy of exclusion. FIG. 20 shows an end cross sectional view of a preferred excluder 300 using compressed air to exclude or clear undesirable entities from the thin web 344, and FIG. 21 shows a cross sectional view taken through section lines 21–21 shown in FIG. 20. FIGS. 22 and 23 are enlarged views of the exclusion zone 150 corresponding to FIGS. 20 and 22, respectively. In the end views, FIGS. 6, 18 and 20, the thin web 320 is seen to be transported through plates 330 and 332 which have a row of inlet nozzles 334 with rectangular apertures 335 whose widths are on the order of three millimeters and are shown in FIG. 20 as having a width D, 338. In the cross sectional view of FIG. 21, the length of the rectangular apertures 335 is shown to be on the order of one centimeter, and the spacing 335 (S) between the apertures is also in the order of one centimeter. The web 320 has a width of approximately one meter or 40 inches, and the row of nozzles 334 extends perpendicularly across the web 320. A single tapered deceleration nozzle 336 having a width of on the order of three millimeters, which is shown in FIG. 20, and a length of a meter is positioned beneath the row of nozzles 334 and receives blasts of air therefrom.

Referring to FIGS. 9, 20 and 21, the row of nozzles 334 is positioned a known distance downstream of the stripes 150 shown in FIG. 9. Since the speed of the web is constantly reported to the computer system 144 by the rotary encoder 168, the computer 144 calculates the time required for any particular segment of the web to pass from, for example, the first one of the stripes 150 to the row of nozzles 334. When an undesirable entity is identified by system 144, its position (spatial coordinates) is determined with respect to the thin web 134 (320 in FIG. 20), and the system 144 calculates the time required for the undesirable entity to reach the row of nozzles. It will be recalled that the CCD arrays 184 in the imaging units 130 and 132 were arranged to view 0.5 mm stripes across the web 134 (320) with each pixel viewing a 0.5 mm rectangle. Thus, by counting pixels across the array to the image of the undesirable entity, the lateral position of the entity is determined. Based on the lateral position of the entity, the computer system 144 also determines which nozzle 334 will be above the entity when it arrives at the nozzles 334. At the appropriate time, when the entity arrives in the exclusion zone 350, a short burst of compressed air is applied to an appropriate one of a plurality of eductor feed pipes 355 by one of the fast acting solenoid valves 157. The computer system 144 applies control signals through control lines 353 to actuate one or more of the valves 353 and release compressed air through the feed pipes 355. Clean compressed air is supplied by pipe 352 to each of the feed pipes 355, and each of the feed pipes is positioned in the mouth 337 of one of the nozzles 334. The compressed air exiting the feed pipe 355 entrains a volumetric flow from a plenum 360 that surrounds the nozzle mouths 337 and defines a chamber that is preferably slightly pressurized, as by compressed air 339. The combined air flow from the feed pipes 355 and the plenum 360 forms a blast of air that strikes and ejects the entity 356 out of the thin web 320, through the decelerating nozzle 336 (FIG. 20), and into a waste pipe 358. The decelerating nozzle 336 is sized to cause a very slight positive initial pressure in the exclusion zone 350, thus pushing the surrounding components of the thin web 320 away from the exclusion zone 350 while at the same time blasting the undesired entity 356 into the waste collection pipe 358. After the initial positive pressure, when the compressed air from feed pipe 335 is turned off, there is a short interval of negative pressure caused by the momentum of the moving air in the decelerating nozzle 336 which causes the components surrounding the exclusion region (a rectangle of about 1 cm×3 mm) to move inwardly; this negative pressure interval is timed to close the exclusion hole in the web 320 but to not pull the web 344 into the waste collection pipe 158.

Air is continuously moving through waste collection pipe 358 to transport the undesirable entities out of the system.

Waste collection pipe 358 and inlet plenum 360 are sized to not interfere with the independent operation of the nozzles 334 and 336, of which there are about one hundred for a web from typical card. Furthermore, the supply air pipe 360 is sufficiently large that the interaction of the short pulse of any one of the exclusion nozzles 334 does not materially affect any of the others, even when more than one of these nozzles 334 is operating simultaneously. The air entering supply pipe 360 is filtered and otherwise conditioned to accommodate the purposes of exclusion.

FIG. 22 shows a second type of compressed air excluder 400 suitable for removing entities from clothed cylinders, such as the doffer cylinder 110 of FIG. 6. A preferred location 402 for excluder 400 marked as "X" on FIGS. 6 and 22 is between the image analyzer system 50 and the crush rolls 122. Referring now to FIG. 22, the image analyzer system 50 Finds and Identifies an entity on the doffer cylinder 110 which is to be excluded, said pattern recognition, decisions and timing being handled by computer 144 in FIG. 8, and control signals on lines 146 which cause excluder controller 404 to energize fast-acting solenoid valve 406. This action supplies clean compressed air to plenum 408 and to blast air orifice 410. Simultaneously, (or separately, with another value and with different timing, if desired) solenoid valve 406 supplies clean compressed air to coaxial eductor 420. Assuming that blast air flow 412 and eductor driven air flow 416 start simultaneously, it is clear that the combined actions of pressure-driven blast air flow 412 and suction driven eductor air flow 416 are to "push and pull" a small volume or "pulse" of air, moving at high speed, across doffer wire 422 in a direction that permits the entity 418 and a few associated fibers 419 to be lifted off wire 422 and pulled into collector pipe 424. Flow 414 is driven by entrainment with flow 412 and by suction associated with flow 416. To summarize, the excluder 400 action may be thought of as providing a short duration (milliseconds) rapidly moving (near Mach 1) volumetric pulse (10's of cubic centimeters) which sweeps the entities off the cylinder wire and excludes them from the web. The width and length of the excluder orifices is about 3 mm×10 mm, like the excluder 300 of FIGS. 18–21, and there are also 100 of them across the one meter width of the web on the doffer cylinder 110.

Compressed air exclusion nozzles are illustrated in this preferred embodiment but other exclusion means may be used as functionally equivalent. Such means include mechanical punching, cutting, or hooking, or the like. While it is preferred to use the system 148 to Find and Identify the features of interest, such as trash in a moving cotton web, it should be understood that other detection systems could be used in conjunction with the excluder. Likewise, other excluders or fiber processors could be used with the detection system described herein.

The various embodiments described herein are intended as examples illustrating the present invention and it will be understood that the present invention is capable of numerous rearrangements, modifications and substitution of parts without departing from the scope of the invention as defined in the appended claims.

What is claimed is:

1. An apparatus for monitoring a web of textile material, said web including a plurality of entities, comprising:

an imaging unit for receiving electromagnetic radiation from said web and producing image signals in response thereto, said image signals corresponding to images of portions of said web including said entities, said web being in motion relative to said imaging unit, said imaging unit for scanning stripe images at first and second fixed locations simultaneously in a direction substantially perpendicular to the direction of relative motion of said web and scanning successive stripe images at said first and second fixed locations at subsequent times while said web is in motion past said fixed locations to produce a plurality of first stripe images and a plurality of second stripe images, such that each stripe image from the first location is produced at a different time from each of the other stripe images from the first location and further such that each of the stripe images from the first location depicts a different portion of the web as compared to other stripe images from the first location, and such that each stripe image from the second location is produced at a different time from each of the other stripe images from the second location and further such that each of the stripe images from the second location depicts a different portion of the web as compared to other stripe images from the second location; and processing means for receiving said image signals from said imaging units, for producing and storing digital data corresponding to the image signals received from said imaging unit, said processing means further comprising means for producing and storing digital data corresponding to a first composite image generated by sequentially accessing each of the plurality of said first stripe images and for producing and storing digital data corresponding to a second composite image generated by sequentially accessing each of the plurality of said second stripe images, said processing means further comprising means for analyzing the digital data, for finding entities of interest in said web based on the analysis of the digital data, for determining parameters of said found entities of interest, and for producing output signals indicating parameters of entities of interest in said web.

2. The apparatus of claim 1 wherein said imaging unit further comprises:

distinguishing means for producing a first set of optical images of the web at the first location from the received electromagnetic radiation, each of said optical images of the first set being distinguished one from the others by the spectral content of the images; and distinguishing means for producing a second set of optical images of the web at the second location from the received electromagnetic radiation, each of said optical images of the second set being distinguished one from the others by the spectral content of the images, said first set being separate from said second set.

3. The apparatus of claim 2 wherein said processing means further comprises means for identifying an entity of interest as an undesirable entity based on the spectral content of the entity.

4. The apparatus of claim 1 wherein said imaging unit further comprises:

a mask having at least first and second slits formed therein disposed for receiving electromagnetic radiation from the web, for blocking portions of the electromagnetic radiation, and for transmitting a plurality of at least first and second spatially separated stripes of the electromagnetic radiation through said slits, said plurality of at least first and second spatially separated stripes of radiation corresponding to said first and second fixed locations from which said plurality of first stripe images and said plurality of second stripe images are produced;

imaging optics for directing and focusing the spatially separated stripes of the electromagnetic radiation;

spectral separation means for separating each of the at least first and second spatially separated stripes of electromagnetic radiation into at least first and second spatially and spectrally separated stripes, each of said first and second spatially and spectrally separated stripes being composed of a plurality of side-by-side spectral rows having different spectral content;

an array of detectors;

said imaging optics for focusing images of the first and second spatially and spectrally separated stripes onto said array of detectors as said plurality of first stripe images and said plurality of second stripe images;

said array of detectors for producing the image signals corresponding to the first and second spatially and spectrally separated stripes;

said processing means for receiving the image signals, for producing digital data based on the image signals, for storing data corresponding to each spatially and spectrally separated stripe in the same position of different memory locations and for storing data corresponding to different spectral rows in different memory locations.

5. The apparatus of claim 1 wherein said imaging unit further comprises:

a mask having at least first and second slits formed therein disposed for receiving electromagnetic radiation from the web, for blocking portions of the electromagnetic radiation, and for transmitting a plurality of at least first and second spatially separated stripes of the electromagnetic radiation through said slits, said plurality of at least first and second spatially separated stripes of radiation corresponding to said first and second fixed locations from which said plurality of first stripe images and said plurality of second stripe images are produced;

imaging optics for directing and focusing the spatially separated stripes of the electromagnetic radiation;

spectral separation means for separating each of the at least first and second spatially separated stripes of electromagnetic radiation into at least first and second spatially and spectrally separated stripes, each of said first and second spatially and spectrally separated stripes being composed of a plurality of side-by-side spectral rows having different spectral content; and an array of detectors;

said imaging optics for focusing images of the first and second spatially and spectrally separated stripes onto said array of detectors as said plurality of first stripe images and said plurality of second stripe images;

said array of detectors for producing the image signals corresponding to the first and second spatially and spectrally separated stripes;

wherein said processing means produces the digital data in the form of books of data in memory, each book having a plurality of pages and each page having a plurality of rows of data, said processing means storing data corresponding to each spatially and spectrally separated stripe on the same row of different pages and storing data corresponding to different spectral rows on different pages.

6. The apparatus of claim 1 wherein said imaging unit further comprises:

a mask having at least first and second slits formed therein disposed for receiving electromagnetic radiation from the web, for blocking portions of the electromagnetic radiation, and for transmitting a plurality of at least first and second spatially separated stripes of the electromagnetic radiation through said slits, said plurality of at least first and second spatially separated stripes of radiation corresponding to said first and second fixed locations from which said plurality of first stripe images and said plurality of second stripe images are produced;

imaging optics for directing and focusing the spatially separated stripes of the electromagnetic radiation, the positions of said first and second stripes being defined by said mask and imaging optics; and an array of detectors;

said imaging optics for focusing images of the first and second spatially separated stripes onto said array of detectors as said first and second stripe images;

said array of detectors for producing the image signals corresponding to the first and second spatially separated stripes.

7. The apparatus of claim 6 wherein said processing means further comprises means for averaging the first and second composite images to produce an average digital representation.

8. The apparatus of claim 6 wherein said processing means further comprises means for comparing the first and second composite images to produce a comparison output indicating characteristics of entities of the web.

9. The apparatus of claim 6 wherein said imaging unit further comprises:

a source of illumination for providing successive first and second conditions of illumination at said first and second fixed locations respectively while the web is in motion past said fixed locations;

said detector producing a first condition image during the first condition of illumination and a second condition image during the second condition of illumination.

10. The apparatus of claim 9 wherein said processing means compares said digital representations of said first and second condition images and classifies entities of interest.

11. The apparatus of claim 9 further comprising:

said illumination means for illuminating one side of the web and reflecting light from the web toward the imaging unit to produce the first illumination condition, which is a reflected illumination condition, and for illuminating the other side of the web and transmitting light through the web to produce the second illumination condition, which is a transmitted illumination condition.

12. The apparatus of claim 9 further comprising:

said illumination means for illuminating one side of the web and reflecting light from the web toward the imaging unit to produce the first illumination condition, which is a reflected illumination condition, and for illuminating the other side of the web and transmitting light through the web to produce the second illumination condition, which is a transmitted illumination condition;

said processing means for producing a first web image based on a plurality of said first condition images, producing a second web image based on a plurality of second condition images, comparing said first and second web images, for finding and classifying entities of interest based upon the comparing, for determining first and second apparent sizes of an entity of interest based upon the first and second web images, respectively, and for determining that the entity of interest is composed of fiber when the first apparent size is greater than the second apparent size by a predetermined amount.

13. The apparatus of claim 12 further comprising:

said processing means for determining whether the first apparent size is within a predetermined range and identifying an entity of interest as corresponding to a nep if the first apparent size is within the predetermined range and the first apparent size is greater than the second apparent size by a predetermined amount.

14. The apparatus of claim 1 further comprising:

said processing means for determining the apparent shape of the entities of interest based on the analysis of the digital data and classifying the entities of interest as to type based at least in part on the apparent shape.

15. The apparatus of claim 1 further comprising:

said processing means for determining the apparent size of the entities of interest based on the analysis of the digital data and classifying the entities of interest as to type based at least in part on the apparent size.

16. The apparatus of claim 1 further comprising:

said processing means for determining the apparent color of the entities of interest based on the analysis of the digital data and classifying the entities of interest as to type based at least in part on the apparent color.

17. The apparatus of claim 1 further comprising:

said processing means for determining the position of the entities of interest based on the analysis of the digital data and producing output signals including information as to entity position.

* * * * *